United States Patent
Yavorsky et al.

(10) Patent No.: US 10,532,165 B2
(45) Date of Patent: Jan. 14, 2020

(54) FLUID RESERVOIR AND SYSTEMS FOR FILLING A FLUID RESERVOIR OF A FLUID INFUSION DEVICE

(71) Applicant: MEDTRONIC MINIMED, INC., Northridge, CA (US)

(72) Inventors: Matthew William Yavorsky, Granada Hills, CA (US); Anatoly Aleksandrovich, Encino, CA (US); Edmond W. Yu, Granada Hills, CA (US); Theodore Wilkening, Bowie, MD (US)

(73) Assignee: Medtronic MiniMed, Inc., Northridge, CA (US)

( * ) Notice: Subject to any disclaimer, the term of this patent is extended or adjusted under 35 U.S.C. 154(b) by 205 days.

(21) Appl. No.: 15/419,932

(22) Filed: Jan. 30, 2017

(65) Prior Publication Data
US 2018/0214630 A1   Aug. 2, 2018

(51) Int. Cl.
*A61M 5/36* (2006.01)
*A61M 5/145* (2006.01)
*A61M 5/162* (2006.01)
*A61J 1/20* (2006.01)

(52) U.S. Cl.
CPC ............ *A61M 5/36* (2013.01); *A61M 5/1452* (2013.01); *A61M 5/162* (2013.01); *A61J 1/2013* (2015.05)

(58) Field of Classification Search
CPC ...... A61M 5/1452; A61M 5/36; A61M 5/162; A61J 1/2013; A61J 1/2048; A61J 1/2089; A61J 1/062
See application file for complete search history.

(56) References Cited

U.S. PATENT DOCUMENTS

| | | |
|---|---|---|
| 3,631,847 A | 1/1972 | Hobbs, II |
| 4,212,738 A | 7/1980 | Henne |
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |

(Continued)

FOREIGN PATENT DOCUMENTS

| | | |
|---|---|---|
| DE | 4329229 | 3/1995 |
| EP | 0319268 | 11/1988 |

(Continued)

OTHER PUBLICATIONS

PCT Search Report (PCT/US02/03299), dated Oct. 31, 2002, Medtronic Minimed, Inc.

(Continued)

*Primary Examiner* — Theodore J Stigell
(74) *Attorney, Agent, or Firm* — Lorenz & Kopf, LLP

(57) ABSTRACT

A fluid reservoir for a fluid infusion device is provided. The fluid reservoir includes a first portion that has a first end and a second end. The first end includes a fluid delivery port and at least one bubble retaining feature adjacent to the fluid delivery port. The fluid reservoir includes a second portion received in the second end of the first portion and movable within the first portion from the first end to the second end. The fluid reservoir defines a fluid chamber between the first portion and the second portion.

14 Claims, 17 Drawing Sheets

(56) References Cited

U.S. PATENT DOCUMENTS

| | | |
|---|---|---|
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,364,369 A | 11/1994 | Reynolds |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tackund et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tackund et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |

(56) References Cited

U.S. PATENT DOCUMENTS

| | | |
|---|---|---|
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,396,330 B2 | 7/2008 | Banet et al. |
| 7,621,893 B2 | 11/2009 | Moberg et al. |
| 7,828,764 B2 * | 11/2010 | Moberg ............ A61J 1/1406 604/155 |
| 7,905,868 B2 | 3/2011 | Moberg et al. |
| 2001/0044731 A1 | 11/2001 | Coffman et al. |
| 2002/0013518 A1 | 1/2002 | West et al. |
| 2002/0055857 A1 | 5/2002 | Mault |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0039365 A1 | 2/2004 | Aramata et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2008/0269681 A1 * | 10/2008 | Kavazov ............ A61M 5/1413 604/123 |
| 2008/0269687 A1 | 10/2008 | Chong et al. |
| 2009/0081951 A1 | 3/2009 | Erdmann et al. |
| 2009/0082635 A1 | 3/2009 | Baldus et al. |
| 2009/0299290 A1 | 12/2009 | Moberg |
| 2011/0218511 A1 | 9/2011 | Yokoyama |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.
Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.
Brackenridge B P (1992). Carbohydrate Gram Counting A Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting A Primer for Insulin Pump Users to Zero in on Good Control. MiniMed Inc.
Marcus A O et al. (1996). insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous insulin Infusion [CSII;] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MinMied•Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).

(56) References Cited

OTHER PUBLICATIONS

Disetronic My Choice H-TRONplus Insulin Pump Reference Manual. (no date).
Disetronic H-TRON®plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International; 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analylica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocalalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian. D., et al., "A Telemetry-Instrumentation System for Chronically Implanted Glucose and Oxygen. Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J. et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, at al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.

(56) References Cited

OTHER PUBLICATIONS

Shichiri, M., "A Needle-Type Glucose Sensor—A Valuable Tool Not Only for a Self-Blood Glucose Monitoring but for a Wearable Aitiffical Pancreas," Life Support Systems Proceedings, XI Annual Meeting ESAO, Alpbach-Innsbruck, Austria, Sep. 1984, pp. 7-9.
Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.
Shichiri, Motoaki, el al., "Closed-Loop Glycemic Control with a Wearable Artificial Endocrine Pancreas—Variations in Daily insulin Requirements to Glycemic Response," Diabetes, vol. 33, Dec. 1984, pp. 1200-1202.
Shichiri, Motoaki, et al., "Glycaemic Control in a Pacreatectomized Dogs with a Wearable Artificial Endocrine Pancreas," Diabetologia, vol. 24, 1983, pp. 179-184.
Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.
Shichiri, M., et al., "Membrane design for extending the long-life of an implantable glucose sensor," Diab. Nutr. Metab., vol. 2, No. 4, 1989, pp. 309-313.
Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.
Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.
Shichiri, Motoaki, et al., "Wearable Artificial Endocrine Pancreas with Needle-Type Glucose Sensor," The Lancet, Nov. 20, 1982, pp. 1129-1131.
Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.
Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.
Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.
Sternberg, Robert, et al., "Study and Development of Multilayer Needle-type Enzyme-based Glucose Microsensors," Biosensors, vol. 4, 1988, pp. 27-40.
Tamiya, E., et al., "Micro Glucose Sensors using Electron Mediators Immobilized on a Polypyrrole-Modified Electrode," Sensors and Actuators. vol. 18, 1989, pp. 297-307.
Tsukagoshi, Kazuhiko, et al., "Specific Complexation with Mono- and Disaccharides that can be Detected by Circular Dichroism," J. Org. Chem., vol. 56, 1991, pp. 4089-4091.
Urban, G., et al., "Miniaturized multi-enzyme biosensors integrated with pH sensors on flexible polymer carriers for in vivo applciations," Biosensors & Bioelectronics, vol. 7, 1992, pp. 733-739.
Ubran, G., et al., "Miniaturized thin-film biosensors using covalently immobilized glucose oxidase," Biosensors & Bioelectronics, vol. 6, 1991, pp. 555-562.
Velho, G., et al., "In vivo calibration of a subcutaneous glucose sensor for determination of subcutaneous glucose kinetics," Diab. Nutr. Metab., vol. 3, 1988, pp. 227-233.
Wang, Joseph, et al., "Needle-Type Dual Microsensor for the Simultaneous Monitoring of Glucose and Insulin," Analytical Chemistry, vol. 73, 2001, pp. 844-847.
Yamasaki, Yoshimitsu, et al., "Direct Measurement of Whole Blood Glucose by a Needle-Type Sensor," Clinics Chimica Acta, vol. 93, 1989, pp. 93-98.
Yokoyama, K., "Integrated Biosensor for Glucose and Galactose," Analytica Chimica Acta, vol. 218, 1989, pp. 137-142.

* cited by examiner

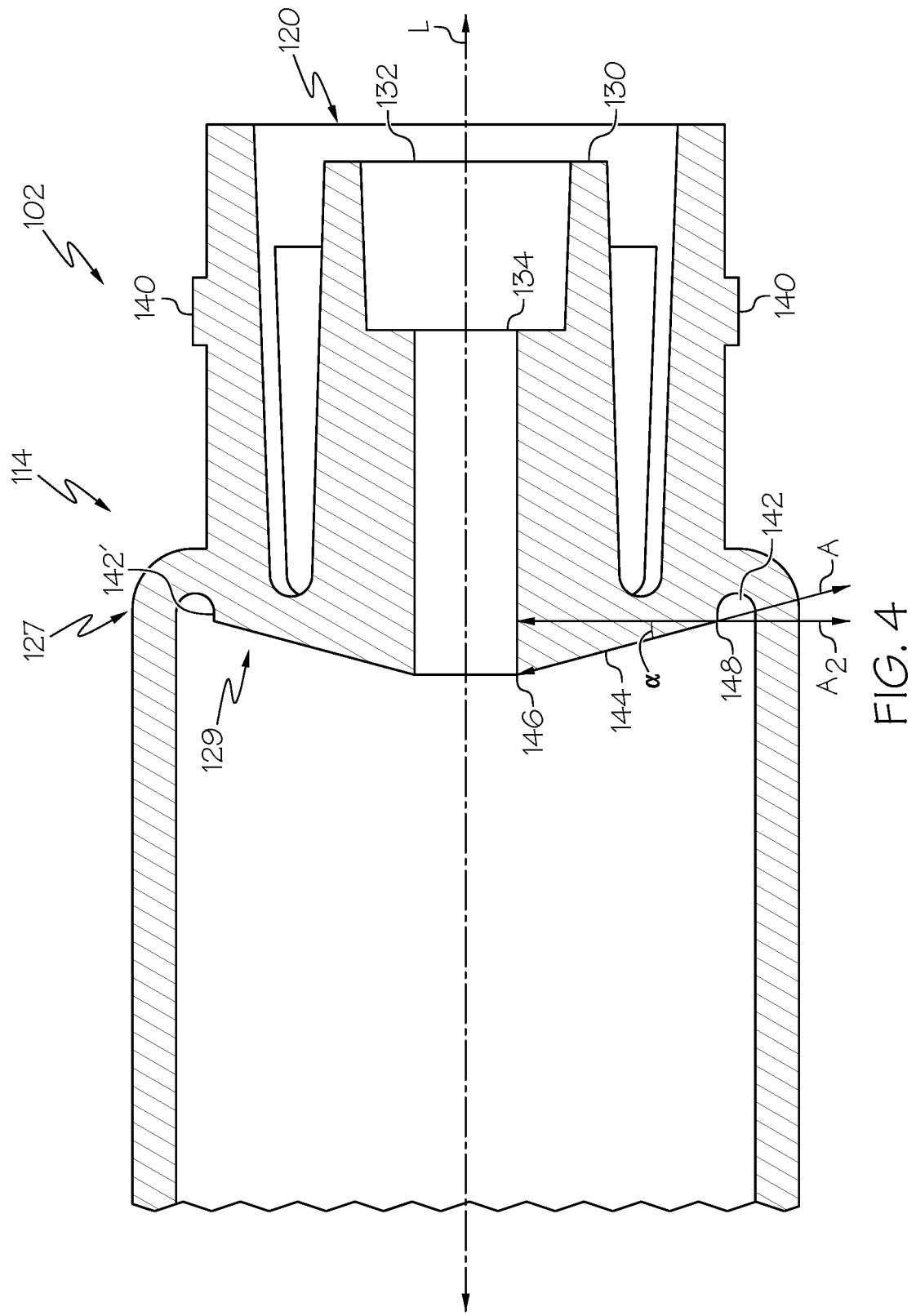

FLUID RESERVOIR AND SYSTEMS FOR FILLING A FLUID RESERVOIR OF A FLUID INFUSION DEVICE

TECHNICAL FIELD

Embodiments of the subject matter described herein relate generally to fluid infusion devices for delivering a medication fluid to the body of a user. More particularly, embodiments of the subject matter relate to a fluid reservoir for a fluid infusion device and systems for filling the fluid reservoir of the fluid infusion device.

BACKGROUND

Certain diseases or conditions may be treated, according to modern medical techniques, by delivering a medication or other substance to the body of a user, either in a continuous manner or at particular times or time intervals within an overall time period. For example, diabetes is commonly treated by delivering defined amounts of insulin to the user at appropriate times. Some common modes of providing insulin therapy to a user include delivery of insulin through manually operated syringes and insulin pens. Other modern systems employ programmable fluid infusion devices (e.g., insulin pumps) to deliver controlled amounts of insulin to a user.

A fluid infusion device suitable for use as an insulin pump may be realized as an external device or an implantable device, which is surgically implanted into the body of the user. External fluid infusion devices include devices designed for use in a generally stationary location (for example, in a hospital or clinic), and devices configured for ambulatory or portable use (to be carried by a user). External fluid infusion devices may establish a fluid flow path from a fluid reservoir to the patient via, for example, a set connector of an infusion set, which is coupled to the fluid reservoir. In many instances, the fluid reservoir requires filling by the patient prior to use in the external fluid infusion device. This process can be tedious and time consuming. In addition, many set connectors of various infusion sets have one or more vent ports near where the fluid reservoir connects to the set connector. In certain instances, the filling of the fluid reservoir with the fluid prior to use may result in wetting of these vent ports of the set connector, which is undesirable. In other scenarios, air may be trapped during the filling of the fluid reservoir. Trapped air may form "bubbles" within the fluid contained in the fluid reservoir, which are also undesirable.

Accordingly, it is desirable to provide improved systems for filling a fluid reservoir of a fluid infusion device, and a fluid reservoir that can be filled with a reduced occurrence of wetting of the vent ports. Moreover, it is desirable to provide a fluid reservoir that reduces an amount of trapped air or "bubbles" that enter and exit the fluid reservoir. Furthermore, other desirable features and characteristics will become apparent from the subsequent detailed description and the appended claims, taken in conjunction with the accompanying drawings and the foregoing technical field and background.

BRIEF SUMMARY

A system for filling a fluid reservoir of a fluid infusion device with a fluid is provided. In one embodiment, the system includes the fluid reservoir having a first portion and a second portion. A fluid chamber is defined between the first portion and the second portion. The second portion is movable within the first portion and includes an interface. The system includes a transfer guard having a first end and a second end. The first end to be coupled to a source of the fluid and the second end having at least one locking member that couples to the interface. The transfer guard defines a fluid flow path for the fluid from the source, and the transfer guard is movable relative to the first portion to fill the fluid chamber with the fluid.

Also provided is a system for filling a fluid reservoir of a fluid infusion device with a fluid. The system includes the fluid reservoir having a barrel portion and a plunger portion. A fluid chamber is defined between the barrel portion and the plunger portion. The plunger portion is movable within the barrel portion and includes an interface having at least one locking projection. The system includes a transfer guard having a first end and a second end. The first end to be coupled to a source of the fluid. The second end includes at least one locking member that couples to the at least one locking projection of the interface to couple the transfer guard to the fluid reservoir and at least one piercing member that defines a fluid flow path from the source of the fluid to the fluid chamber. The transfer guard is movable relative to the barrel portion to fill the fluid chamber with the fluid.

Further provided is a fluid reservoir for a fluid infusion device. The fluid reservoir includes a first portion that has a first end and a second end. The first end includes a fluid delivery port and at least one bubble retaining feature adjacent to the fluid delivery port. The fluid reservoir includes a second portion received in the second end of the first portion and movable within the first portion from the first end to the second end. The fluid reservoir defines a fluid chamber between the first portion and the second portion.

Also provided is a fluid reservoir for a fluid infusion device. The fluid reservoir includes a barrel portion that has a first end and a second end. The first end includes a fluid delivery port and at least one bubble retaining feature. The fluid reservoir includes a plunger portion received in the second end of the barrel portion and movable within the barrel portion from the first end to the second end. The fluid reservoir also includes a fluid chamber defined between the barrel portion and the plunger portion, and the at least one bubble retaining feature is disposed within the fluid chamber.

Further provided is a fluid reservoir for a fluid infusion device. The fluid reservoir includes a barrel portion that has a first end and a second end. The first end includes an end wall having a first surface and a second surface. The first surface includes a fluid delivery port and the second surface defines a ramp. An annular groove is defined about a perimeter of the second surface. The ramp and the annular groove cooperate to retain bubbles within the fluid reservoir. The fluid reservoir also includes a plunger portion having a monolithic stopper received in the second end of the barrel portion and movable within the barrel portion from the first end to the second end. The fluid reservoir includes a fluid chamber defined between the barrel portion and the plunger portion.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 4 is a detail cross-sectional view of a portion of the fluid reservoir, taken from 4 of FIG. 3;

DETAILED DESCRIPTION

Figure 1:
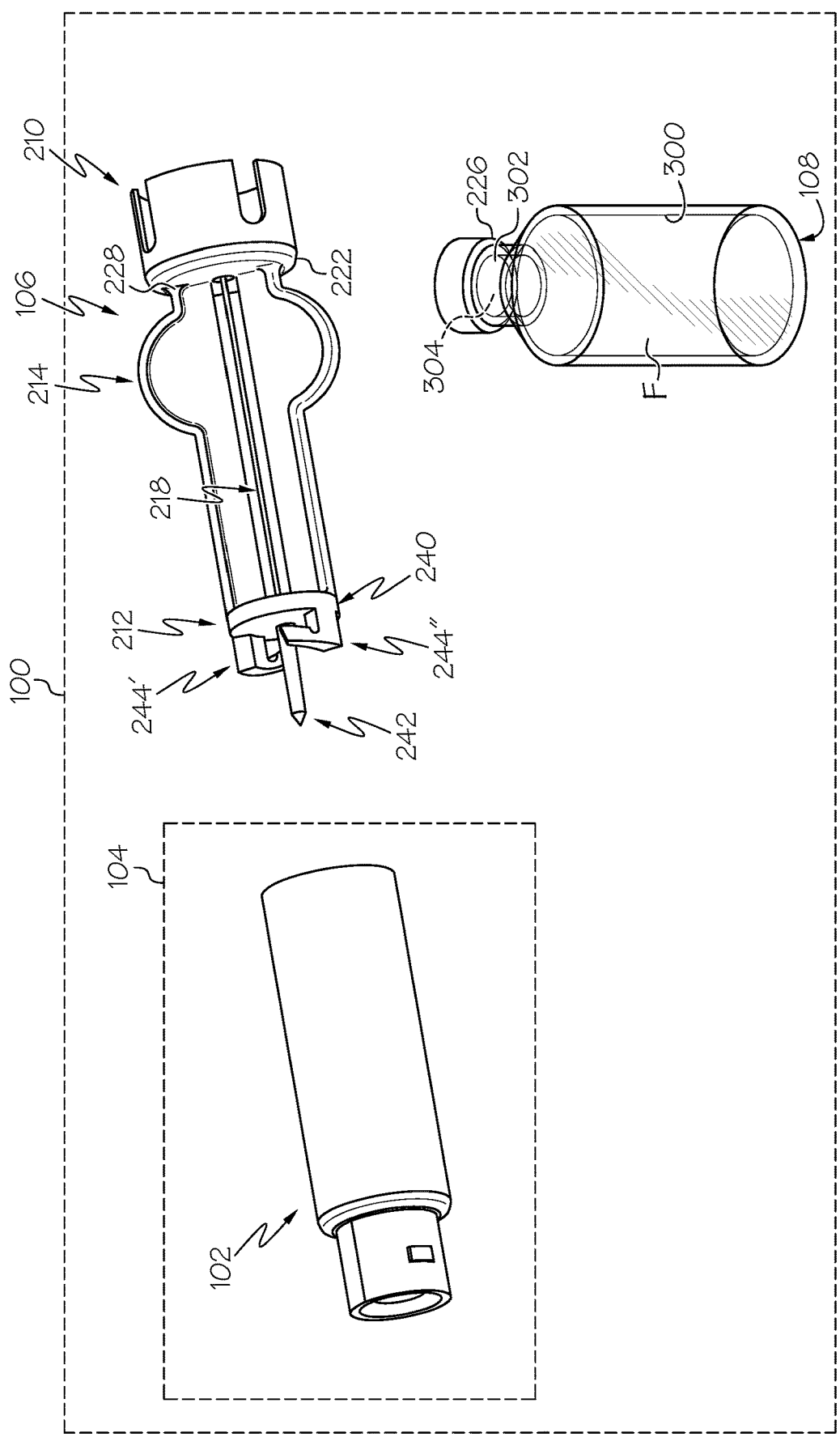
FIG. 1 is a perspective view of an exemplary fluid reservoir of a fluid infusion device and an exemplary system for filling the fluid reservoir of the fluid infusion device according to various teachings of the present disclosure.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

As used herein, the term "axial" refers to a direction that is generally parallel to or coincident with an axis of rotation, axis of symmetry, or centerline of a component or components. For example, in a cylinder or disc with a centerline and generally circular ends or opposing faces, the "axial" direction may refer to the direction that generally extends in parallel to the centerline between the opposite ends or faces. In certain instances, the term "axial" may be utilized with respect to components that are not cylindrical (or otherwise radially symmetric). For example, the "axial" direction for a rectangular housing containing a rotating shaft may be viewed as a direction that is generally parallel to or coincident with the rotational axis of the shaft. Furthermore, the term "radially" as used herein may refer to a direction or a relationship of components with respect to a line extending outward from a shared centerline, axis, or similar reference, for example in a plane of a cylinder or disc that is perpendicular to the centerline or axis. In certain instances, components may be viewed as "radially" aligned even though one or both of the components may not be cylindrical (or otherwise radially symmetric). Furthermore, the terms "axial" and "radial" (and any derivatives) may encompass directional relationships that are other than precisely aligned with (e.g., oblique to) the true axial and radial dimensions, provided the relationship is predominately in the respective nominal axial or radial direction. As used herein, the term "transverse" denotes an axis that crosses another axis at an angle such that the axis and the other axis are neither substantially perpendicular nor substantially parallel.

The following description relates to a fluid infusion device of the type used to treat a medical condition of a user. The infusion device can be used for infusing fluid into the body of a user. The non-limiting examples described below relate to a medical device used to treat diabetes (more specifically, an insulin pump), although embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump and/or infusion set operation, fluid reservoirs, and fluid syringes may not be described in detail here. Examples of infusion pumps and/or related pump drive systems used to administer insulin and other medications may be of the type described in, but not limited to: U.S. Patent Publication Nos. 2009/0299290 and 2008/0269687; U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; 7,621,893; 7,828,764; and 7,905,868; which are each incorporated by reference herein.

FIG. 1 is a perspective view of an exemplary embodiment of a fluid transfer system or system 100 for filling a fluid reservoir 102 of a fluid infusion device 104. The system 100 includes the fluid reservoir 102 of the fluid infusion device 104, a transfer device or guard 106 and a vial 108. One or more components of the system 100 can be packaged together in suitable packaging for use as a kit by a consumer or user. The system 100 enables the user to fill the fluid reservoir 102 of the fluid infusion device 104 with all or a portion of the contents of the vial 108 while reducing a risk of wetting one or more vent ports associated with the infusion set coupled to the fluid reservoir 102 and while reducing an amount of trapped air or "bubbles" that exit the fluid reservoir 102, as will be discussed in greater detail herein.

The fluid infusion device 104 may be any fluid infusion device known in the art, and thus, the fluid infusion device 104 will not be discussed in great detail herein. In one example, the fluid infusion device 104 is an insulin infusion device, such as the MiniMed Paradigm® REAL-Time Revel™ Insulin Pump, MiniMed 630G Insulin Pump or MiniMed 670G Insulin Pump, each commercially available from Medtronic MiniMed, Inc. of Northridge, Calif. Briefly, the fluid infusion device 104 is designed to be carried or worn by the patient. The fluid infusion device 104 may leverage a number of conventional features, components, elements, and characteristics described in U.S. Pat. Nos. 6,485,465 and 7,621,893, the relevant content of which is incorporated by reference herein.

Figure 2:
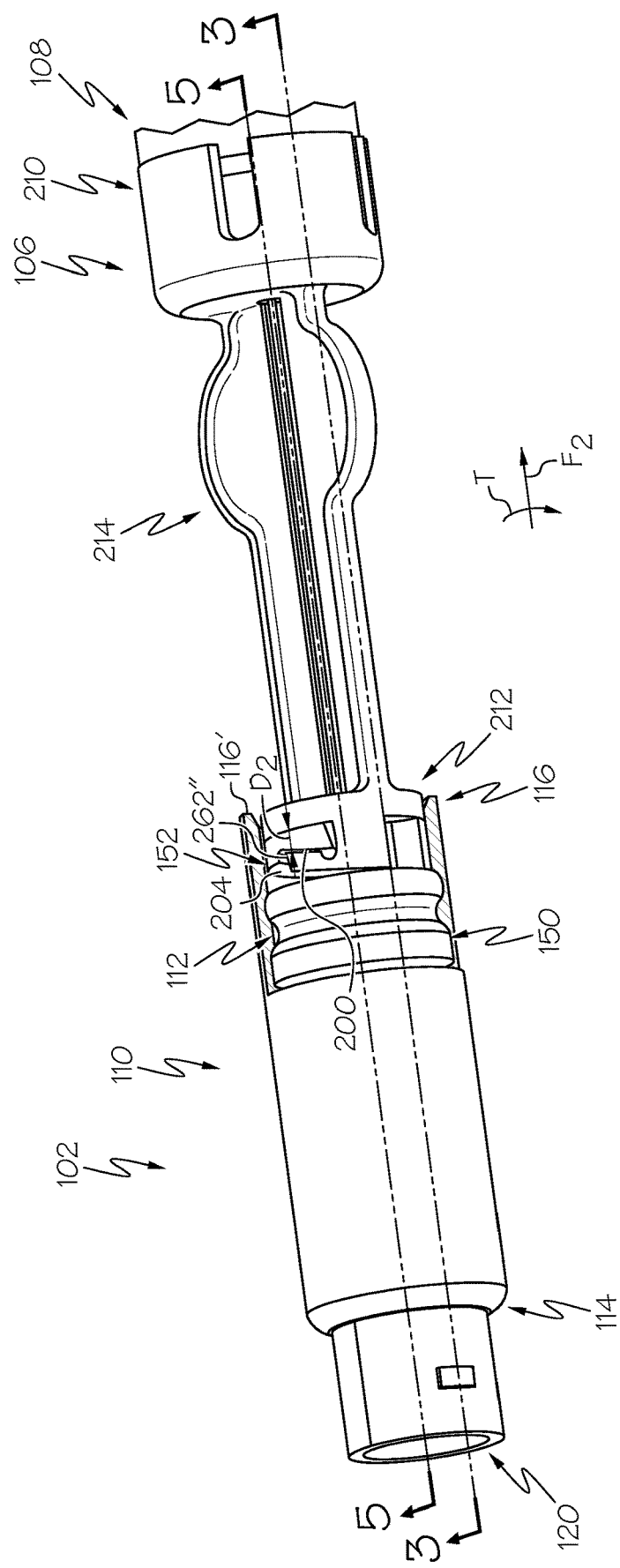
FIG. 2 is perspective view of the system of FIG. 1 assembled to fill the fluid reservoir of the fluid infusion device, with a pair of locking members of a transfer guard in a second position.

The fluid reservoir 102 is removably coupled to the fluid infusion device 104. With reference to FIG. 2, a partial cut-away view of the fluid reservoir 102 is shown coupled to the transfer guard 106. The fluid reservoir 102 includes a first portion or barrel portion 110 and a second portion or plunger portion 112. Generally, with reference to FIG. 3, the barrel portion 110 includes a first end 114, a second end 116 and a fluid chamber or reservoir 118 defined between the first end 114 and the second end 116. The barrel portion 110 may be composed of a biocompatible polymer, and may be injection molded, etc.

In one example, the first end 114 of the barrel portion 110 includes a delivery port 120, a coupling flange 122 and one or more bubble retaining features 124. In this example, the delivery port 120 and the coupling flange 122 cooperate to couple the fluid reservoir 102 to a set connector of an infusion set for establishing a fluid flow path out of the fluid reservoir 102. In one example, the set connector and infusion set comprise the Sure-T Paradigm® Infusion Set, which is commercially available from Medtronic MiniMed, Inc. of Northridge, Calif. Generally, the delivery port 120 and the coupling flange 122 are defined on a first side 125 of an end wall 127 at the first end 114, and the bubble retaining features 124 are defined on a second side 129 of the end wall 127. The first side 125 is generally opposite the second side 129, and the end wall 127 defines a first terminal end of the reservoir 118.

The delivery port 120 establishes a fluid flow path from the reservoir 118. In this example, the delivery port 120 is substantially cylindrical, and includes an exterior surface 126 and an interior bore 128. The exterior surface 126 may also define a swaged flange 130, which aids in retaining the septum 136 within the delivery port 120. The interior bore 128 includes a septum chamber 132 and a needle passage 134. The septum chamber 132 is defined at a first end of the interior bore 128 and is surrounded by the flange 130, which encloses a portion of the first end of the interior bore 128, thereby enclosing a portion of the septum chamber 132. Generally, the flange 130 extends radially inward about a perimeter of the septum chamber 132 to retain a septum 136 within the septum chamber 132. The septum chamber 132 receives the septum 136, which serves to prevent the ingress and egress of fluids out of the reservoir 118. The septum 136 is pierceable with a piercing member of the set connector (not shown) to enable fluid flow out of the reservoir 118. Generally, the piercing member is received through the needle passage 134. The needle passage 134 extends from the septum chamber 132 to the reservoir 118, and receives the piercing member to enable fluid communication between the reservoir 118 and the infusion set (not shown). The needle passage 134 may include tapered sidewalls to assist in forming the needle passage 134 and in retaining the septum 136 within the septum chamber 132.

The coupling flange 122 substantially surrounds or circumscribes the delivery port 120. The coupling flange 122 includes one or more projections 140, which are defined on an exterior surface of the delivery port 120. The projections 140 generally extend outwardly from the exterior surface, and cooperate with the set connector of the infusion set to securely couple the infusion set to the fluid reservoir 102. It will be understood that the use of projections 140 is merely exemplary, as any engagement feature may be defined on the coupling flange 122 that cooperates with the set connector.

The bubble retaining features 124 are defined on the end wall 127 of the first end 114. Thus, the bubble retaining features 124 are disposed within the reservoir 118. In this example, the bubble retaining features 124 include the second side 129 of the end wall 127 and an annular trap 142. In this regard, the shape of the second side 129 guides trapped air or "bubbles" within the fluid contained within the reservoir 118 to the trap 142 due to the buoyancy of the trapped air. In one example, with reference to FIG. 4, the second side 129 has a surface 144 that extends from an inner end 146 to an outer end 148. In this example, the surface 144 is an inclined or ramp surface, and is generally angled relative to the end wall 127 such that the "bubble" in the reservoir 118 may be guided by the surface 144 to the trap 142 due to the buoyancy of the "bubble" within the reservoir 118. As shown, in cross-section, the surface 144 extends along an axis A that has a negative slope relative to an axis A2 defined through the end wall 127, with the axis A2 substantially perpendicular to a longitudinal axis L of the fluid reservoir 102. The axis A is generally transverse to or oblique to the longitudinal axis L. In one example, an angle α defined between the axis A and the axis A2 is about 15 to about 45 degrees. Stated another way, the surface 144 defines a ramp having a positive slope in a direction of fluid flow out of the delivery port 120 of the fluid reservoir 102. It should be noted that while the surface 144 is illustrated herein as extending substantially along a line in cross-section, the surface 144 may be contoured and may be substantially convex, if desired.

Figure 4A:
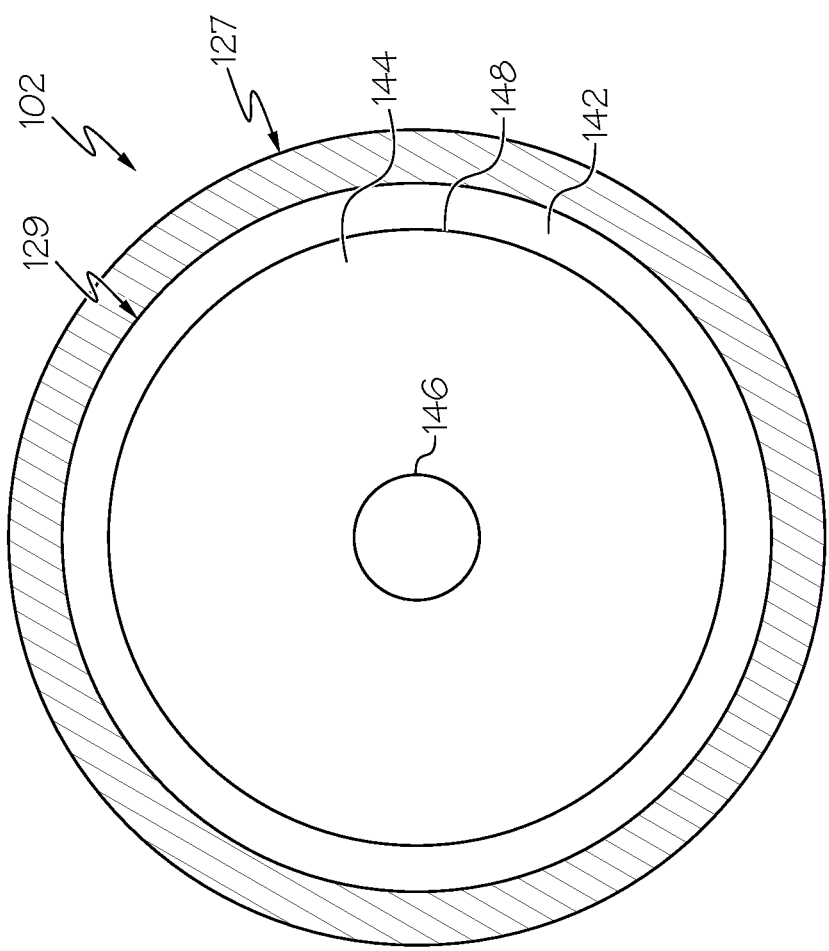
FIG. 4A is a detail cross-sectional end view of the portion of the fluid reservoir of FIG. 4, which illustrates an annular trap defined about a perimeter of an end wall of the fluid reservoir.

The trap 142 is an annular groove or recess defined about a perimeter of the end wall 127 within the reservoir 118, as shown in FIG. 4A. With reference to FIG. 4, the trap 142 may have a substantially U-shaped cross-section, and may include a sharp corner 142' at the transition from the outer end 148 of the surface 144, which aids in retaining any "bubbles" within the trap 142, and thus, the reservoir 118. It will be understood, however, that the trap 142 may have any desired cross-sectional shape.

Figure 3:
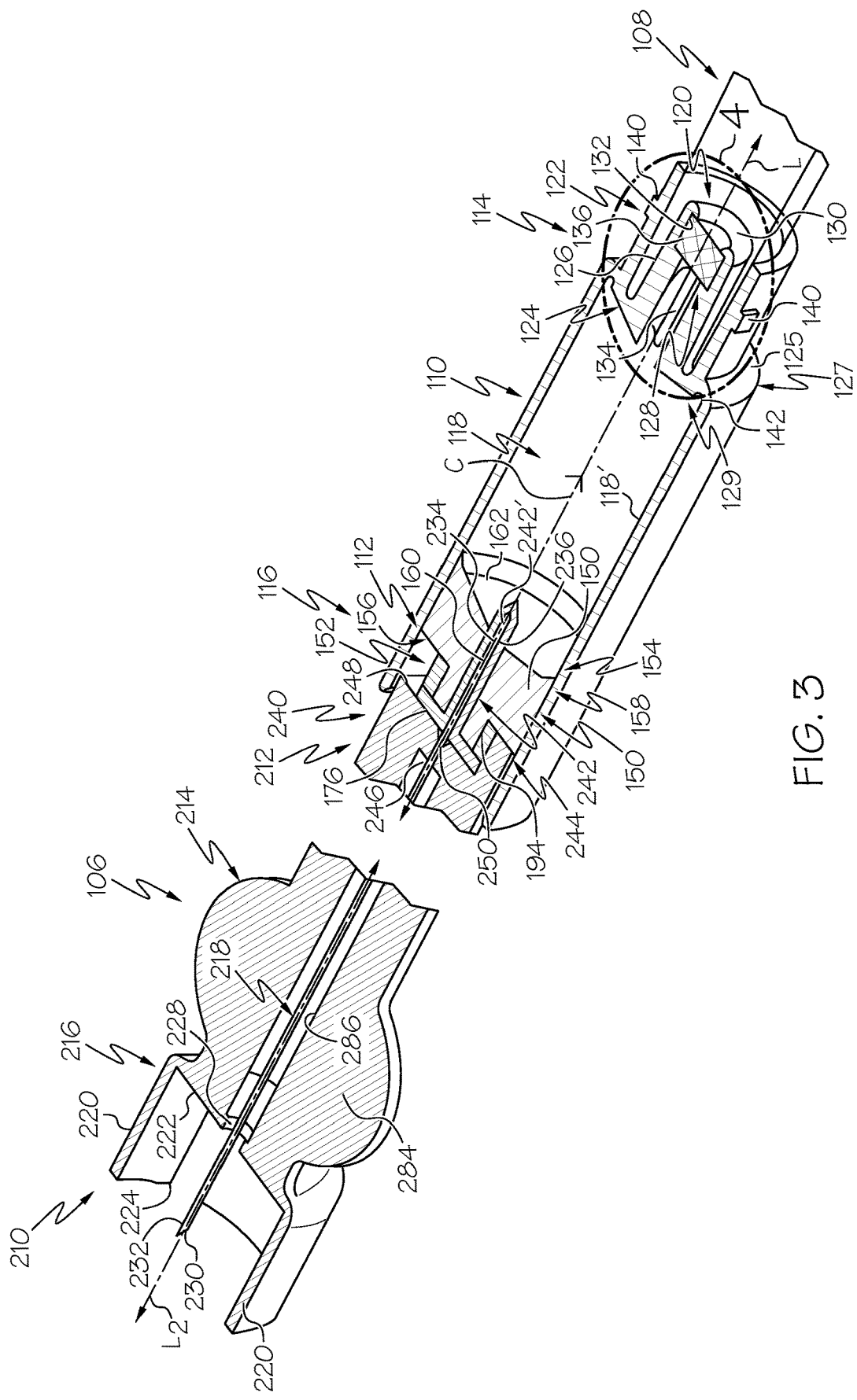
FIG. 3 is a cross-sectional view of the system of FIG. 2, taken along line 3-3 of FIG. 2, with a plunger portion of the fluid reservoir shown in a first position.

With reference to FIG. 3, the second end 116 of the fluid reservoir 102 is substantially circumferentially open, and cooperates with the stopper 150. The reservoir 118 is defined between the first end 114 and the second end 116. As will be discussed in greater detail below, the reservoir 118 is fillable with a fluid F from the vial 108 (FIG. 1) using the transfer guard 106. In this example, the reservoir 118 is fillable with insulin from the vial 108, but the reservoir 118 can be fillable with any suitable liquid.

The plunger portion 112 is received within the second end 116 of the fluid reservoir 102 and is movable by a drive system of the fluid infusion device 104 within the reservoir 118 to dispense fluid from the reservoir 118 through the set connector (not shown). In this example, the plunger portion 112 includes a stopper 150 and an interface 152. As will be discussed, the interface 152 is coupled to the stopper 150, and cooperates with the transfer guard 106 to enable the filling of the reservoir 118 and to enable the movement of the plunger portion 112 upon application of a force from a drive system of the fluid infusion device 104. The interface 152 also provides a rigid contact point for the drive system associated with the fluid infusion device 104.

The stopper 150 is composed of a biocompatible elastomeric material, such as a silicone. The stopper 150 may be molded, cast or formed with any suitable technique. In this example, the stopper 150 is integrally formed or is a one-piece monolithic component. The stopper 150 is substantially symmetric about a central axis C of the stopper 150. The stopper 150 has a body that includes a first stopper end 154, a second stopper end 156, a sidewall 158 and a central slit 160. The stopper 150 is sized and shaped to be received within the second end 116 of the reservoir 118 such that the sidewall 158 forms a seal with a wall 118' of the reservoir 118. The stopper 150 is generally movable within the reservoir 118 from the second end 116 (FIG. 3) to the first end 114 (FIG. 3A) to dispense fluid out of the reservoir 118 via the delivery port 120 and from the first end 114 (FIG. 3A) to the second end 116 (FIG. 3) to fill the reservoir 118 with the fluid F from the vial 108 (FIG. 1).

Figure 3A:
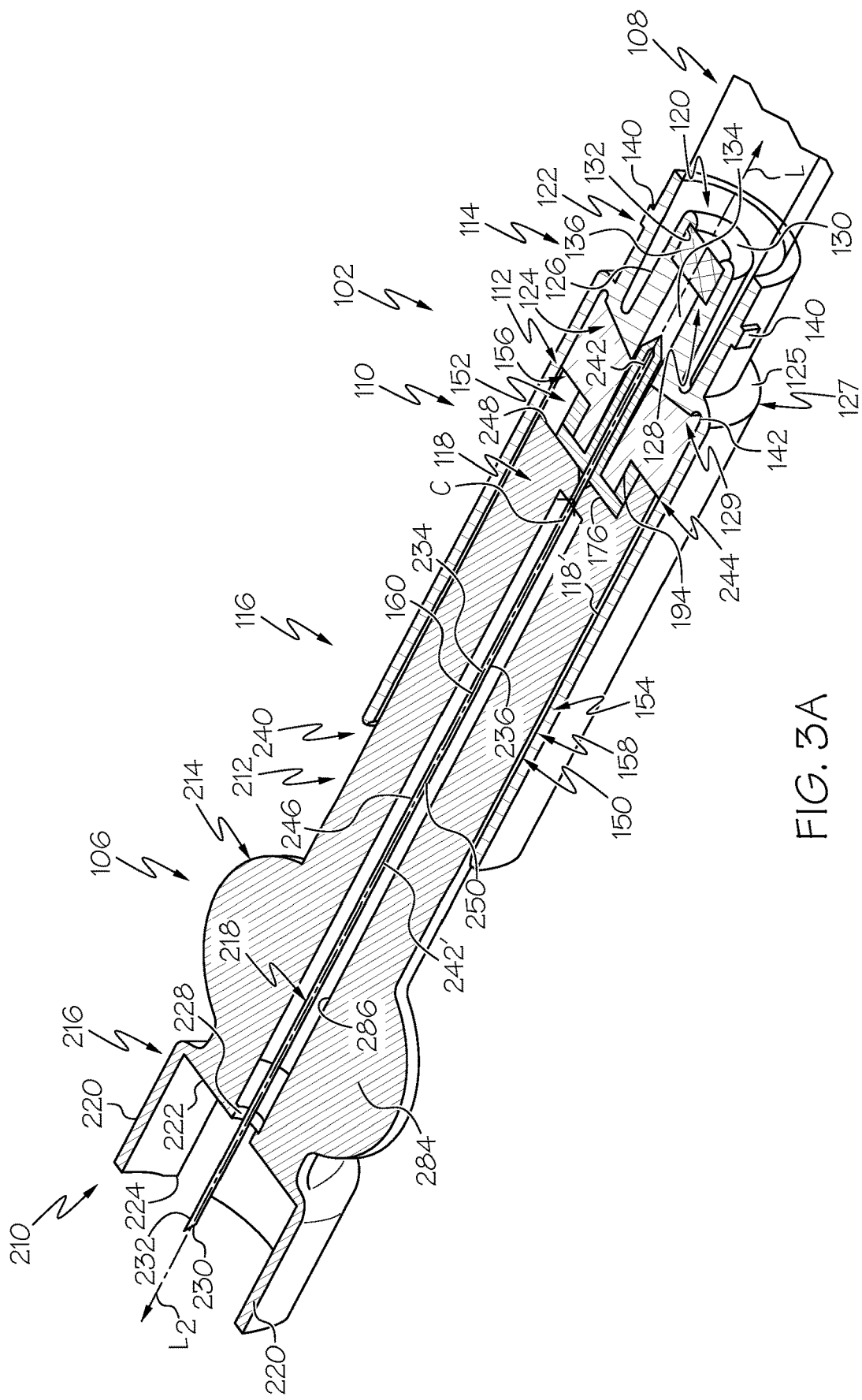
FIG. 3A is a cross-sectional view of the system of FIG. 2, taken along line 3-3 of FIG. 2, with the plunger portion shown in a second position.
Figure 5:
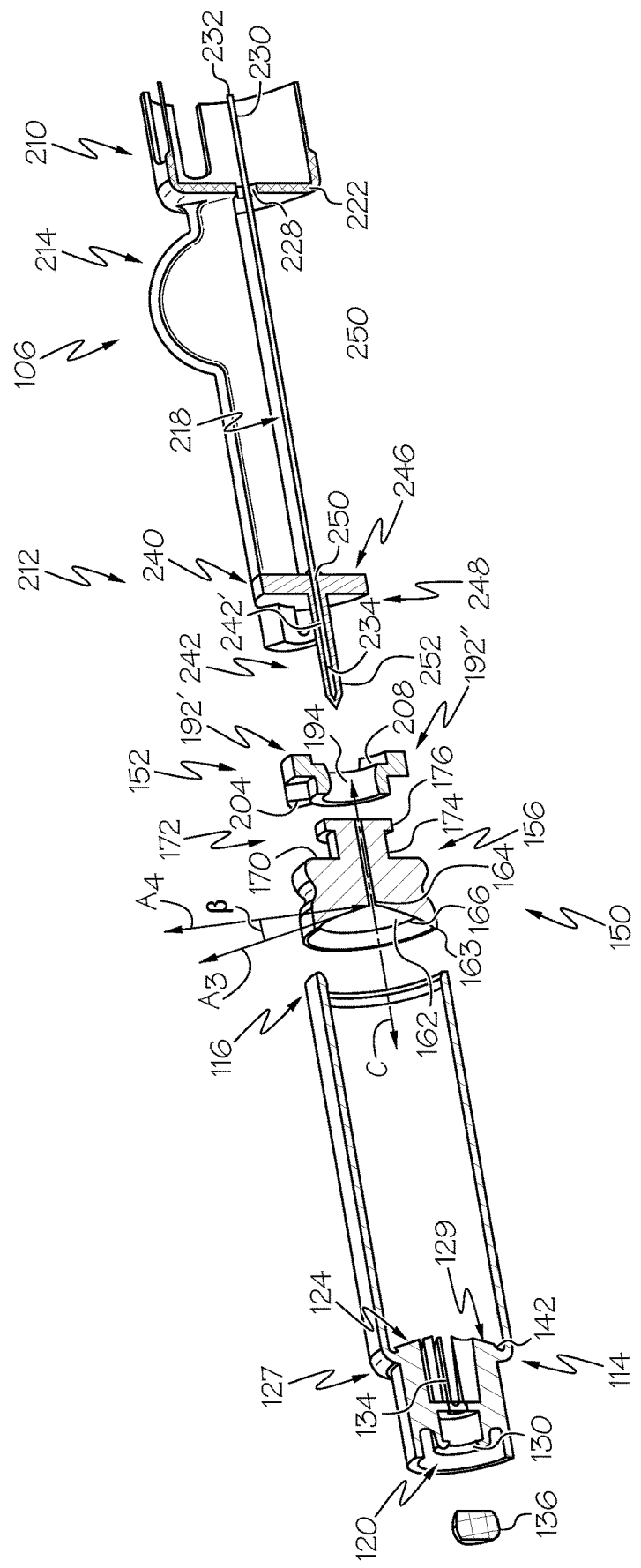
FIG. 5 is an expanded cross-sectional view of the system of FIG. 2, taken along line 5-5 of FIG. 2.

The first stopper end 154 is opposite the second stopper end 156, and faces the first end 114 of the reservoir 118 when the stopper 150 is received within the reservoir 118. The first stopper end 154 includes a first stopper surface 162 and a lip 163. Generally, the first stopper surface 162 has a shape or contour that corresponds to the shape of the second side 129 of the end wall 127. The contour of the first stopper surface 162 enables the first stopper surface 162 to be positioned against and mate with the end wall 127 to empty the fluid F from the reservoir 118; and to be positioned against and mate with the end wall 127 to enable the filling of the reservoir 118 with the fluid F, as shown in FIG. 3A. With reference to FIG. 5, the first stopper surface 162 may extend from a first inner stopper end 164 to a first outer stopper end 166 along an axis A3 in cross-section, and may comprise an inclined surface or a ramp. The axis A3 may be transverse to or oblique to an axis A4 defined through the cross-section of the stopper 150 near the first stopper end 154. The axis A4 is substantially perpendicular to the central axis C of the stopper 150. An angle β may be defined between the axis A3 and the axis A4. In one example, the angle β may be about 15 to about 45 degrees. In this example, the first stopper surface 162 has a positive slope. It should be noted that while the first stopper surface 162 is illustrated herein as extending substantially along a line, the first stopper surface 162 may be contoured and may be substantially concave, if desired.

The lip 163 projects axially from the first stopper surface 162 about a perimeter of the first stopper surface 162. The lip 163 is generally sized to be received within the trap 142 when the stopper 150 is adjacent to the second side 129 of the end wall 127.

The second stopper end 156 couples the stopper 150 to the interface 152. The second stopper end 156 includes a second stopper end surface 170 and a projection 172. The second stopper end surface 170 is substantially planar. In this example, the second stopper end surface 170 extends radially from the projection 172 to the perimeter of the second stopper end 156.

The projection 172 is defined about the central axis C, and includes a base 174 and a flange 176. The base 174 is coupled to the second stopper end surface 170, and extends axially away from the second stopper end surface 170. The base 174 extends for a distance D, which is sized and selected to enable the interface 152 to be positioned about the base 174 to couple the interface 152 to the base 174. The base 174 is generally cylindrical; however, the base 174 may have any desired shape for coupling to the interface 152. The flange 176 is coupled to the base 174. The flange 176 extends radially outward from the base 174 to retain the interface 152. The flange 176 may also be received at least partially within a portion of the transfer guard 106 to aid in coupling the transfer guard 106 to the plunger portion 112.

Figure 6:
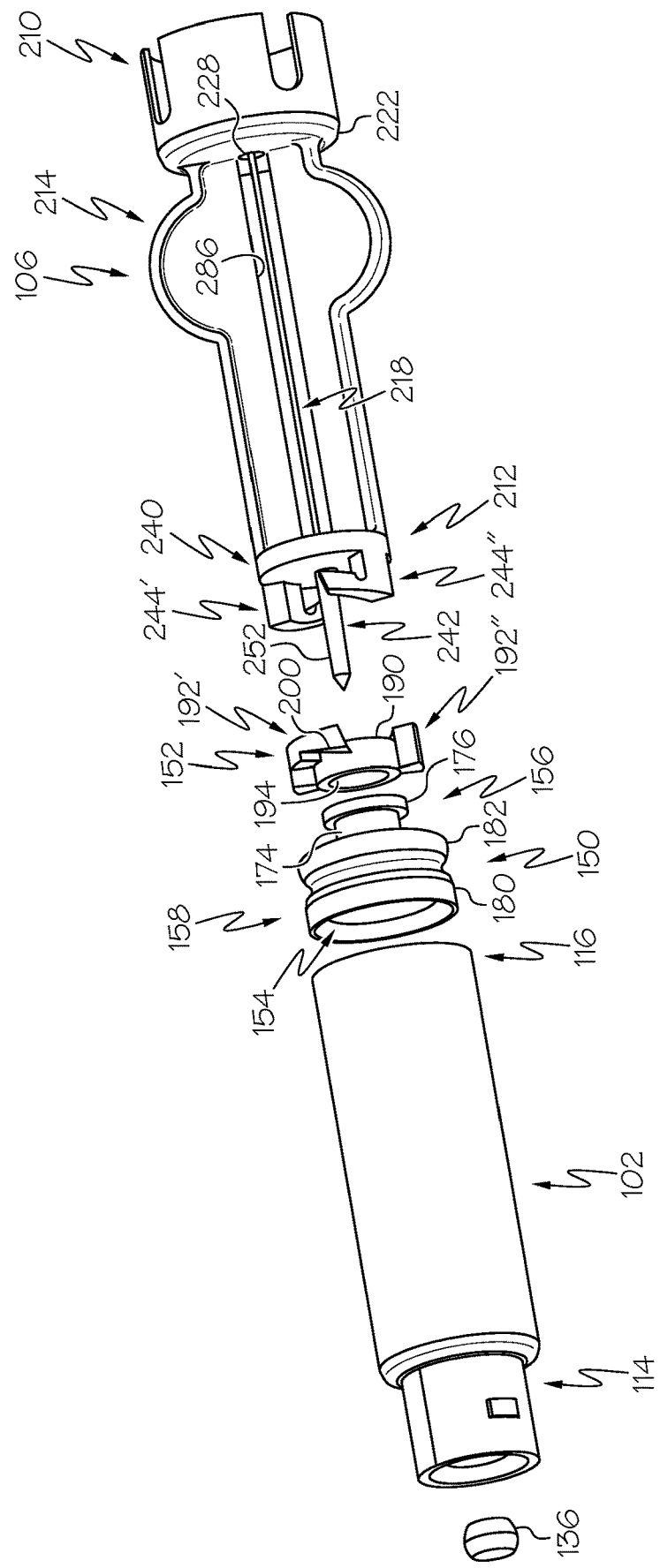
FIG. 6 is an expanded view of the fluid reservoir and the transfer guard in according to the various teachings of the present disclosure.

With reference to FIG. 6, the sidewall 158 extends circumferentially about the stopper 150 from the first stopper end 154 to the second stopper end 156. The sidewall 158 includes a first sealing surface or projection 180 and a second sealing surface or projection 182. Each of the first sealing projection 180 and the second sealing projection 182 may extend radially outward from the sidewall 158 a predetermined distance to engage the wall 118' of the reservoir 118. The first sealing projection 180 and the second sealing projection 182 cooperate to prevent or inhibit fluid exiting the reservoir 118 about the stopper 150. A side of the lip 163 opposite the first stopper surface 162 may form part of the first sealing projection 180, such that the first sealing projection 180 may extend over a greater circumferential area of the stopper 150 than the second sealing projection 182.

The central slit 160 is defined through the body of the stopper 150 such that a portion of the transfer guard 106 may be inserted through the stopper 150 to fill the reservoir 118 with fluid. In this example, the stopper 150 is pre-slit during manufacturing of the stopper 150, via a cutting tool or the like, to enable the portion of the transfer guard 106 to be inserted through the stopper 150. Generally, the central slit 160 is configured such that once the portion of the transfer guard 106 is removed, the material of the stopper 150 substantially closes an opening provided by the central slit 160 to prevent the flow of fluid out of the stopper 150. In this example, the stopper 150 is pre-slit or at least partially cut along the central axis C to form the central slit 160.

Figure 7:
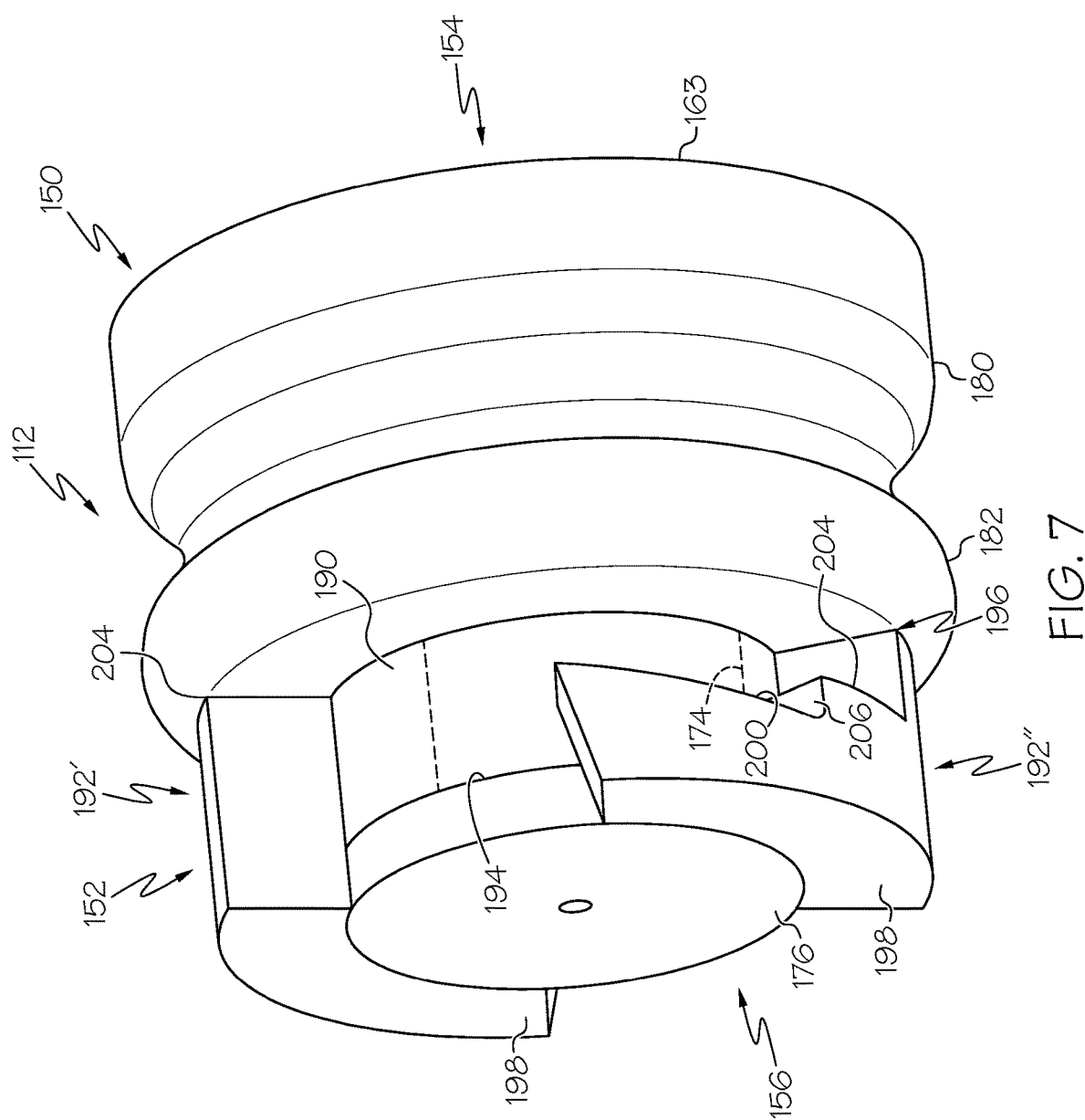
FIG. 7 is a rear perspective view of the plunger portion of the fluid reservoir of FIG. 1, in which a stopper is coupled to an interface.

With reference to FIG. 7, the interface 152 couples the plunger portion 112 to a drive system of the fluid infusion device 104 and the transfer guard 106 (FIG. 1). The interface 152 is rigid, and in one example is composed of a polymer, such as a polycarbonate blend, which is molded, cast, etc. In one example, the interface 152 is coupled to the stopper 150 by molding the interface 152 about the base 174, however, any suitable technique may be employed to couple the interface 152 to the stopper 150. The interface 152 includes an interface body 190, one or more locking projections 192 and an interface bore 194, which is defined through the interface body 190. The interface bore 194 receives the base 174 of the stopper 150 therethrough. Thus, the interface bore 194 has a diameter that is sized to receive the base 174 to couple the interface 152 to the stopper 150.

The interface body 190 is substantially annular, and is sized to be received around the base 174 of the stopper 150 to couple the interface 152 to the stopper 150. The one or more locking projections 192 extend outwardly from the interface body 190, and couple the transfer guard 106 to the plunger portion 112. In this example, the one or more locking projections 192 are a pair of or two projections 192', 192", which cooperate with a portion of the transfer guard 106 to couple the transfer guard 106 to the interface 152. The locking projections 192', 192" each extend radially outward and axially along the interface body 190. The locking projections 192', 192" are substantially opposed or opposite each other about the perimeter or circumference of the interface body 190. The locking projections 192', 192" each include a first projection end 196 substantially opposite a second projection end 198.

Figure 8:
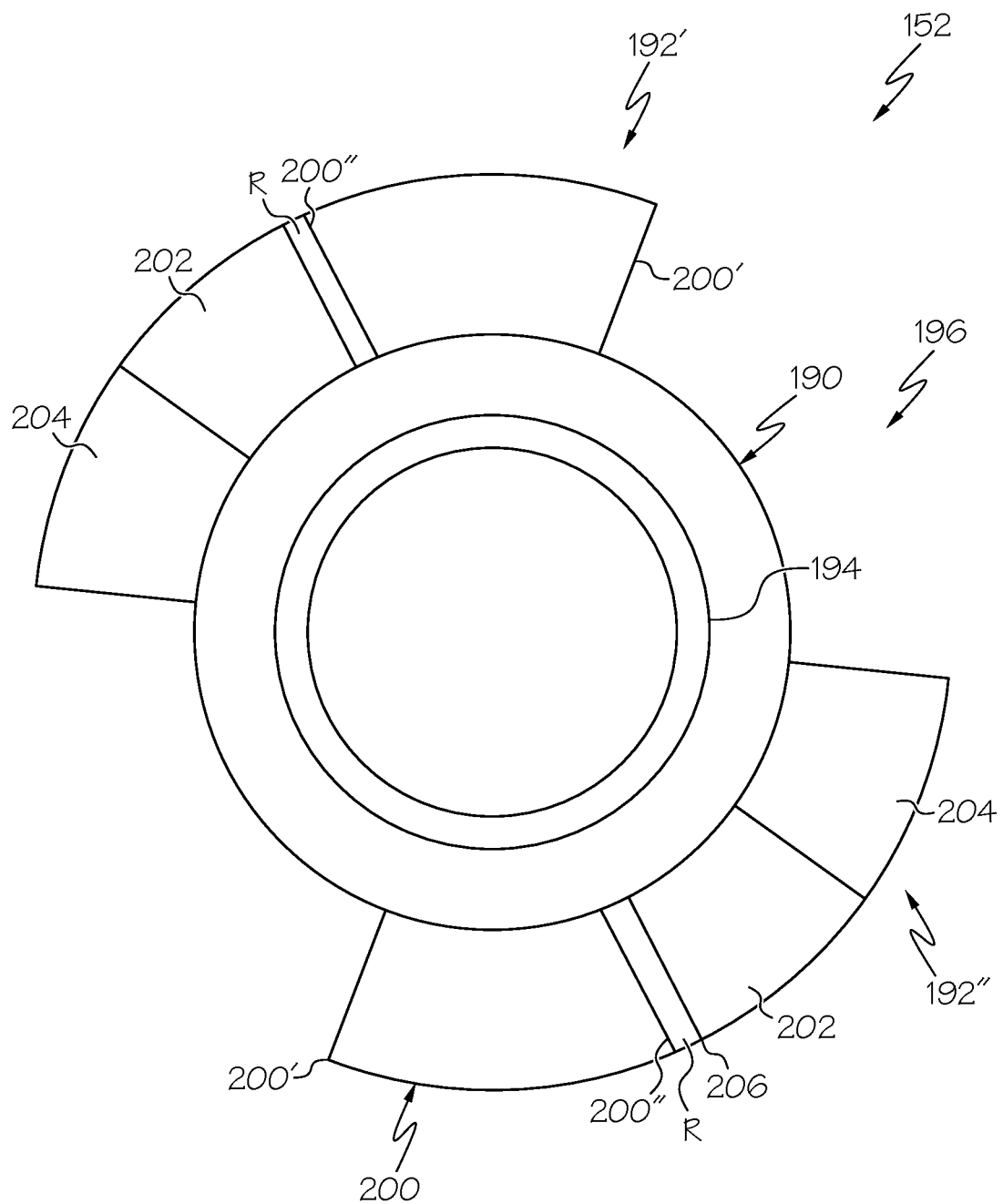
FIG. 8 is a first end view of the interface of the fluid reservoir of FIG. 1.
Figure 9:
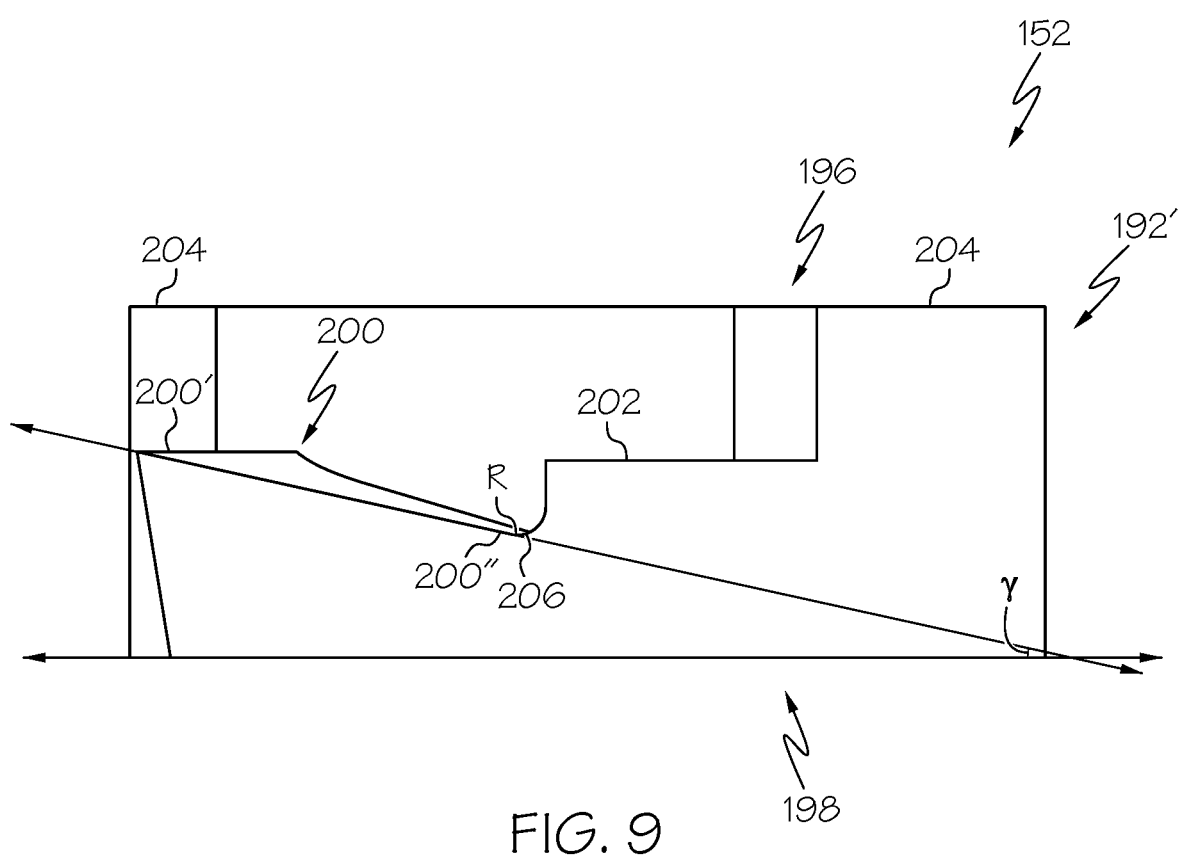
FIG. 9 is a side view of the interface of the fluid reservoir of FIG. 1.

With reference to FIG. 8, the first projection end 196 of each of the locking projections 192', 192" is shown. The first projection end 196 includes a first ramp surface 200, a first ledge surface 202 and a first flange 204. The first ramp surface 200 cooperates with a portion of the transfer guard 106 to enable the coupling and uncoupling of the transfer guard 106 from the plunger portion 112. In one example, with reference to FIG. 9, the first ramp surface 200 extends along an axis A1, which is substantially transverse or oblique to a line L1 that lies along a plane defined by the second projection end 198. In this example, the first ramp surface 200 is at an angle γ of about 5 to about 20 degrees relative to the second projection end 198. It should be noted that the first ramp surface 200 need not extend along a line in cross-section, but rather, may be contoured or curved, depending upon the force requirements necessary for the coupling and uncoupling of the transfer guard 106.

Generally the first ramp surface 200 extends downward from a first ramp end 200' to a second ramp end 200". The first ramp end 200' is a first terminal end of each of the respective locking projections 192', 192" about the perimeter or circumference of the interface body 190. The second ramp end 200" ends at a wall 206, which forms a stop for the further advancement of the portion of the transfer guard 106. In one example, a radius R is defined between the second ramp end 200" and the wall 206. The wall 206 transitions the first projection end 196 to the first ledge surface 202. The first ledge surface 202 is substantially planar or flat, and extends from the wall 206 to the first flange 204. The first ledge surface 202 reduces a mass savings by reducing a thickness of the locking projections 192', 192".

The first flange 204 extends from the first ledge surface 202. Generally, the first flange 204 is defined so as to be contiguous with the interface body 190. With reference back to FIG. 8, the first flange 204 may be substantially wedge-shaped, and the first flanges 204 may be defined about the interface body 190 to substantially opposite each other about the perimeter or circumference of the interface body 190. In this example, the first flanges 204 each define a second terminal end of the respective locking projections 192', 192" about the perimeter or circumference of the interface body 190. Thus, in this example, the first flange 204 of the locking projection 192' is spaced apart from the first ramp end 200' of the locking projection 192", and the first flange 204 of the locking projection 192" is spaced apart from the first ramp end 200' of the locking projection 192'. As shown in FIG. 7, the first flanges 204 contact the second stopper end surface 170 and assist in transferring force from the drive system of the fluid infusion device 104 (FIG. 1) to the stopper 150.

Figure 10:
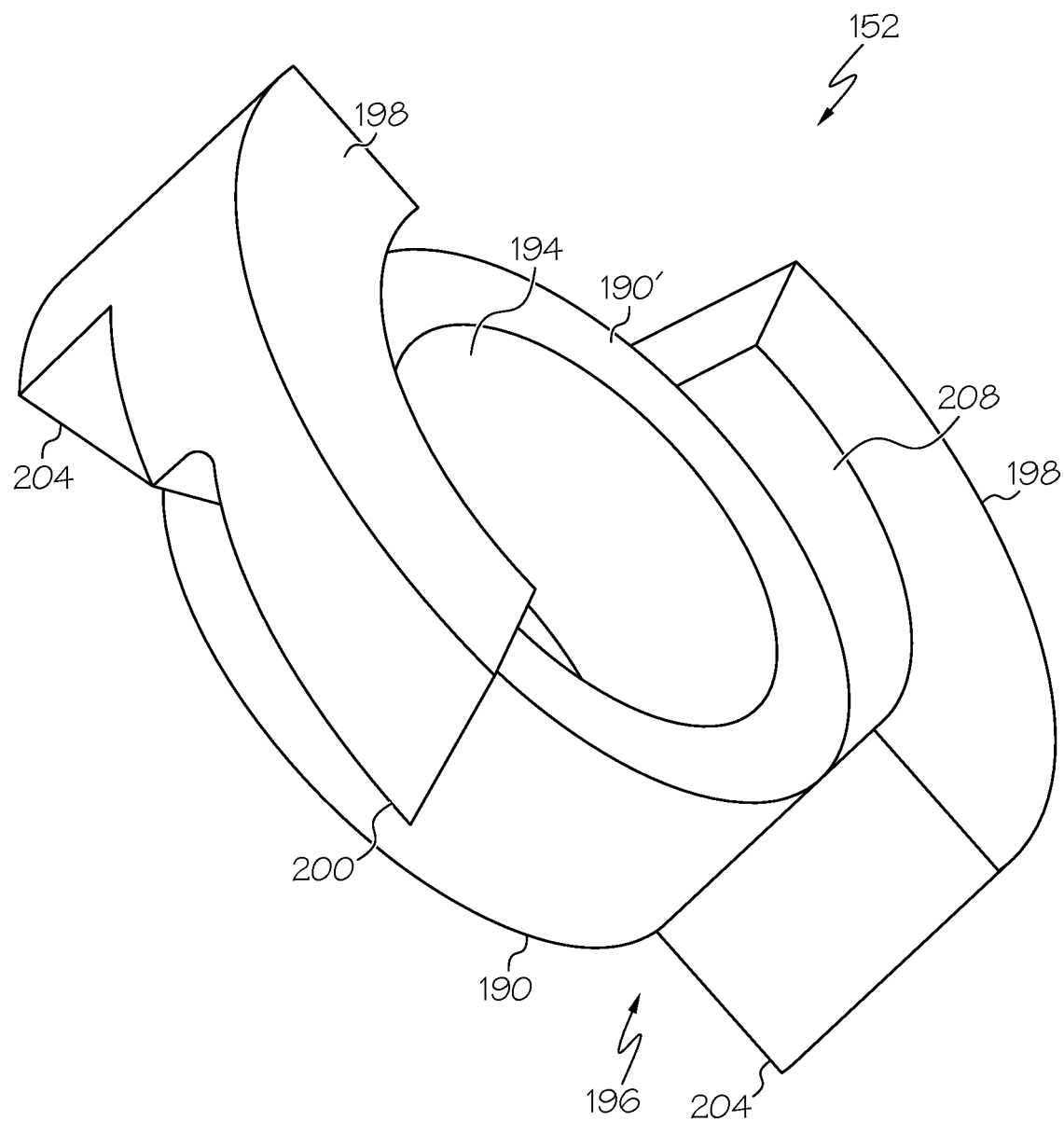
FIG. 10 is a second end view of the interface of the fluid reservoir of FIG. 1.

With reference to FIG. 10, the second projection end 198 of each of the locking projections 192', 192" is shown. The second projection end 198 is planar, and a counterbore 208 is defined between the opposing second projection ends 198. The counterbore 208 is sized and shaped to receive the flange 176 of the stopper 150, such that the flange 176 of the stopper 150 is coplanar with the second projection ends 198. Generally, with reference to FIG. 7, the flange 176 is received within the counterbore 208 such that the flange 176 is coupled to or contacts a surface 190' of the interface body 190. The second projection ends 198 provide a rigid contact surface for the drive system of the fluid infusion device 104 (FIG. 1) such that the application of a drive force to the second projection ends 198 assists in moving the stopper 150 within the second end 116 of the barrel portion 110.

The transfer guard 106 is removably coupled to the fluid reservoir 102 to enable the fluid reservoir 102 to be filled with the fluid F from the vial 108 (FIG. 1). With reference to FIG. 3, the transfer guard 106 is coupled to the fluid reservoir 102 and the vial 108 in a first position, and may be at least partially received within the second end 116 of the fluid reservoir 102. The transfer guard 106 can be composed of any suitable material, such as a biocompatible polymer, for example, a polycarbonate blend, and may be injection molded, cast, etc. The transfer guard 106 includes a first end 210 and a second end 212, which can be interconnected via a body 214.

With reference to FIG. 3, the first end 210 includes a receiving portion 216 and a first piercing member 218. The receiving portion 216 receives a portion of the vial 108 to couple the vial 108 to the transfer guard 106. The receiving portion 216 is illustrated herein as substantially U-shaped in cross-section; however, the receiving portion 216 can have any suitable shape to mate with a portion of the vial 108. In this example, the receiving portion 216 includes one or more projections 220, which are coupled to and extend outwardly from a base 222.

Generally, the projections 220 are spaced apart about a perimeter of the base 222 so as to define one or more apertures 224. The apertures 224 enable a user to visually ensure the vial 108 is properly coupled to the receiving portion 216 and also enable the user to grip the vial 108 through the apertures 224. Generally, the projections 220 extend upwardly from the base 222 so as to extend parallel to a longitudinal axis L2 of the transfer guard 106. The projections 220 cooperate to couple the portion of the vial 108 to the base 222, and thus, the first end 210 of the transfer guard 106.

The base 222 is substantially planar, and the projections 220 extend outwardly from a surface 222a of the base 222. Generally, the projections 220 extend outwardly from a perimeter of the base 222, however, the projections 220 can extend from the base 222 at any desired location based on a circumference or perimeter of a flange 226 of the vial 108. The base 222 also defines a bore 228. The bore 228 is sized and shaped to receive the first piercing member 218 therethrough.

The first piercing member 218 is received through the bore 228 of the base 222. The first piercing member 218 generally extends along the longitudinal axis L2 of the transfer guard 106. The first piercing member 218 may be coupled to the bore 228 through any suitable technique, such as press-fit, adhesive bonding, ultrasonic welding, etc. In one example, the first piercing member 218 is coupled to the bore 228 by an adhesive bond. In one example, the first piercing member 218 comprises a hollow needle or cannula to enable fluid to flow through the first piercing member 218. Generally, the first piercing member 218 is composed of a metal or metal alloy, for example, a stainless steel. The first piercing member 218 has a first piercing tip 230 at a first end 232 and a second conduit tip 234 at a second end 236, with the second end 236 opposite the first end 232. The first piercing tip 230 establishes a fluid flow path out of the vial 108 and through the body 214 of the transfer guard 106. Generally, the projections 220 of the receiving portion 216 generally extend outwardly from the base 222 for a distance greater than the first piercing tip 230 to act as a guard for the first piercing tip 230. The second conduit tip 234 fluidly couples the body 214 to a portion of the second end 212 of the transfer guard 106.

The second end 212 of the transfer guard 106 couples the transfer guard 106 to the interface 152 of the plunger portion 112 of the fluid reservoir 102. Generally, the second end 212 of the transfer guard 106 and the interface 152 cooperate such that the transfer guard 106 may be used only a single time to fill the fluid reservoir 102 with the fluid from the vial 108. Thus, generally, the transfer guard 106 is a consumable component. The second end 212 includes a second base 240, a second piercing member 242 and one or more locking members 244.

Figure 11:
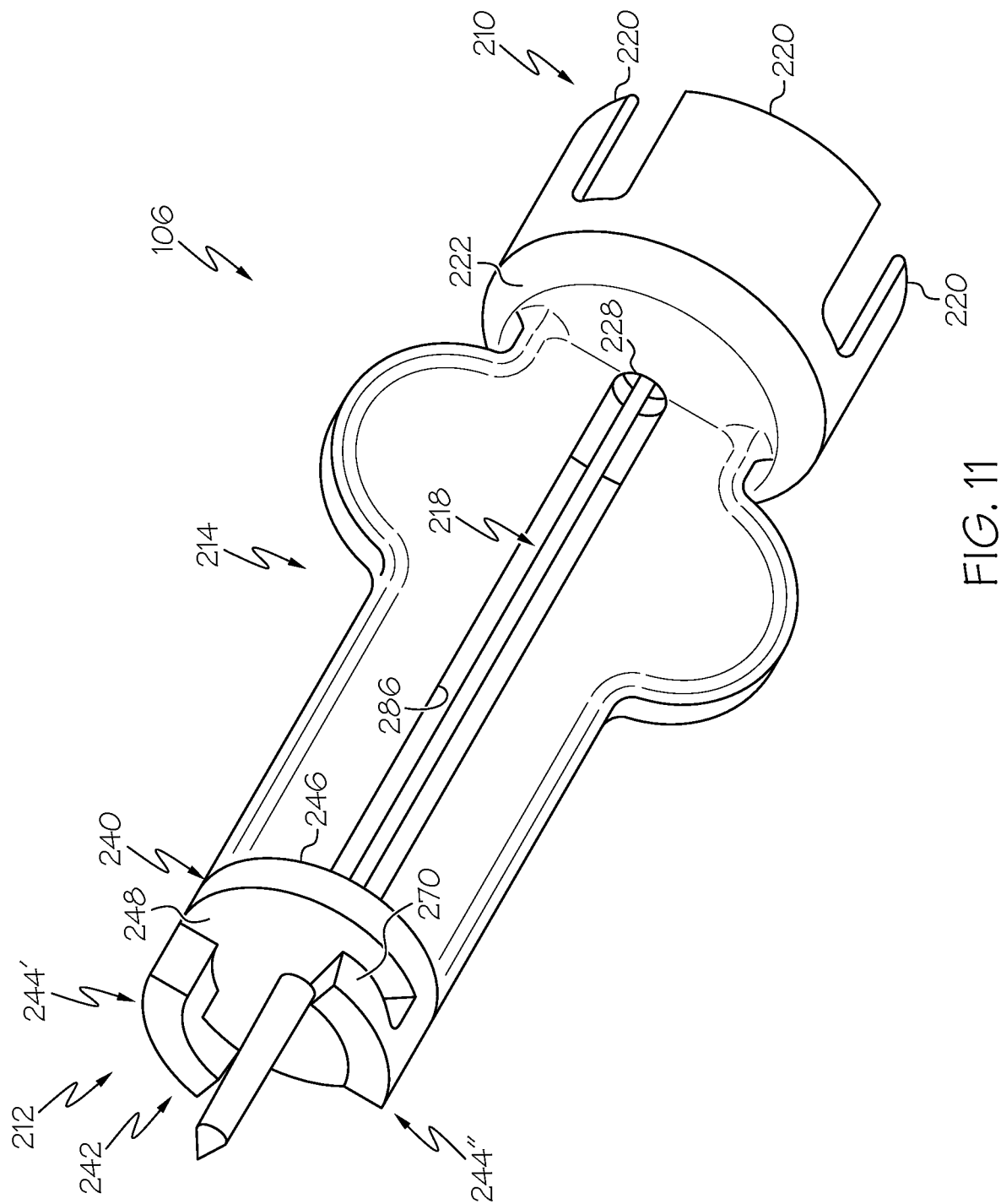
FIG. 11 is a perspective view of the transfer guard of the system of FIG. 1.

With reference to FIGS. 3 and 11, the second base 240 is substantially circular, and includes a first side 246, a second side 248 opposite the first side 246 and defines a second bore 250 (FIG. 3) that extends through the first side 246 and the second side 248. The first side 246 of the second base 240 is coupled to the body 214, and the second side 246 of the second base 240 is coupled to the one or more locking members 244. With reference to FIG. 3, the second bore 250 receives the second conduit tip 234 therethrough. The second piercing member 242 is coupled to the second side 248 of the second base 240 so as to extend outwardly from the second side 248 about a circumference of the second bore 250. The second piercing member 242 has a length, which is sized to enable the second piercing member 242 to be received within the central slit 160 of the stopper 150 such that at least a portion of the second piercing member 242 is received within the reservoir 118 when the transfer guard 106 is coupled to the interface 152 to fill the reservoir 118.

Figure 12:
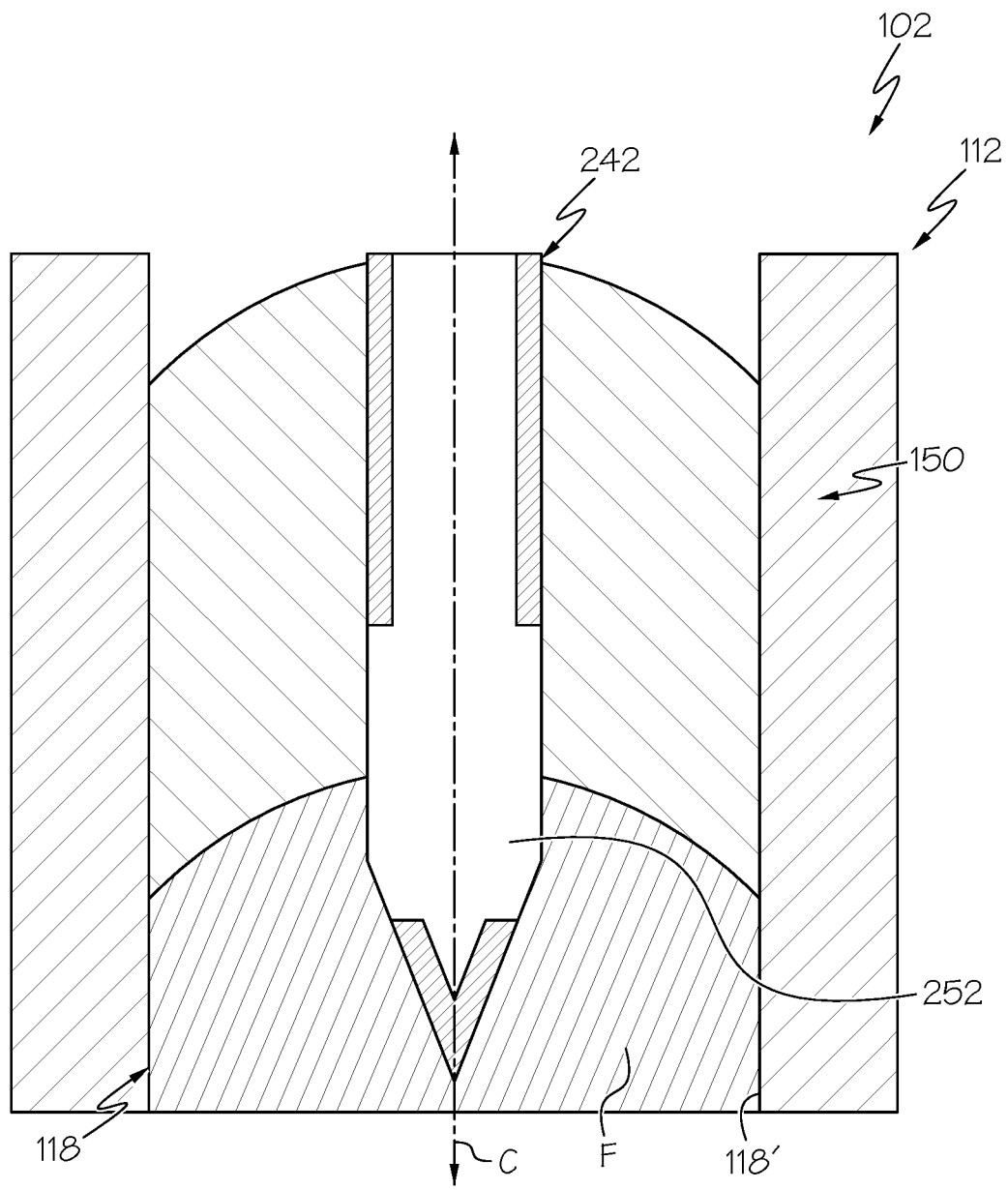
FIG. 12 is an environmental schematic view that illustrates a second piercing member of the transfer guard coupled to the stopper of the fluid reservoir to fill the fluid reservoir with fluid.

The second piercing member 242 generally extends along the longitudinal axis L2 of the transfer guard 106. The second piercing member 242 is generally composed of a biocompatible polymer, such as a polycarbonate blend, and may be integrally formed with the transfer guard 106 or coupled to the transfer guard 106 in a processing step, via ultrasonic welding, for example. The second piercing member 242 is hollow or defines a central bore 242'. The central bore 242' receives the second conduit tip 234 to define a fluid flow path through the transfer guard 106. As shown in FIG. 12, the second piercing member 242 defines a cross-bore 252, which is defined so as to extend through the second piercing member 242 along an axis that is substantially perpendicular to the central axis C of the stopper 150. The cross-bore 252 enables fluid exit the second piercing member 242 into the reservoir 118, and thereby, fill the reservoir 118. The use of a cross-bore 252, the second piercing member 242 composed of a polymeric material and the first inner stopper end 164 having the positive slope in cross-section further assists in reducing an amount of trapped air or "bubbles" that may be introduced during the filling of the reservoir 118 as the concavity defined by the first inner stopper end 164, which is adjacent to the cross-bore 252, may inhibit the trapping of air between the second piercing member 242 and the first stopper end 154 during the filling of the reservoir 118.

With reference to FIG. 11, the one or more locking members 244 are coupled to the second side 248 of the second base 240. In this example, the one or more locking members 244 are a pair of or two locking members 244', 244". Each of the locking members 244', 244" cooperates with a respective one of the locking projections 192', 192", to removably couple the transfer guard 106 to the interface 152 of the plunger portion 112. The locking members 244', 244" are generally opposite or opposed from each other about a perimeter or circumference of the second base 240, and are each spaced apart from the second piercing member 242. Thus, the locking members 244', 244" are spaced apart from or offset from the longitudinal axis L2 of the transfer guard 106.

Figure 13:
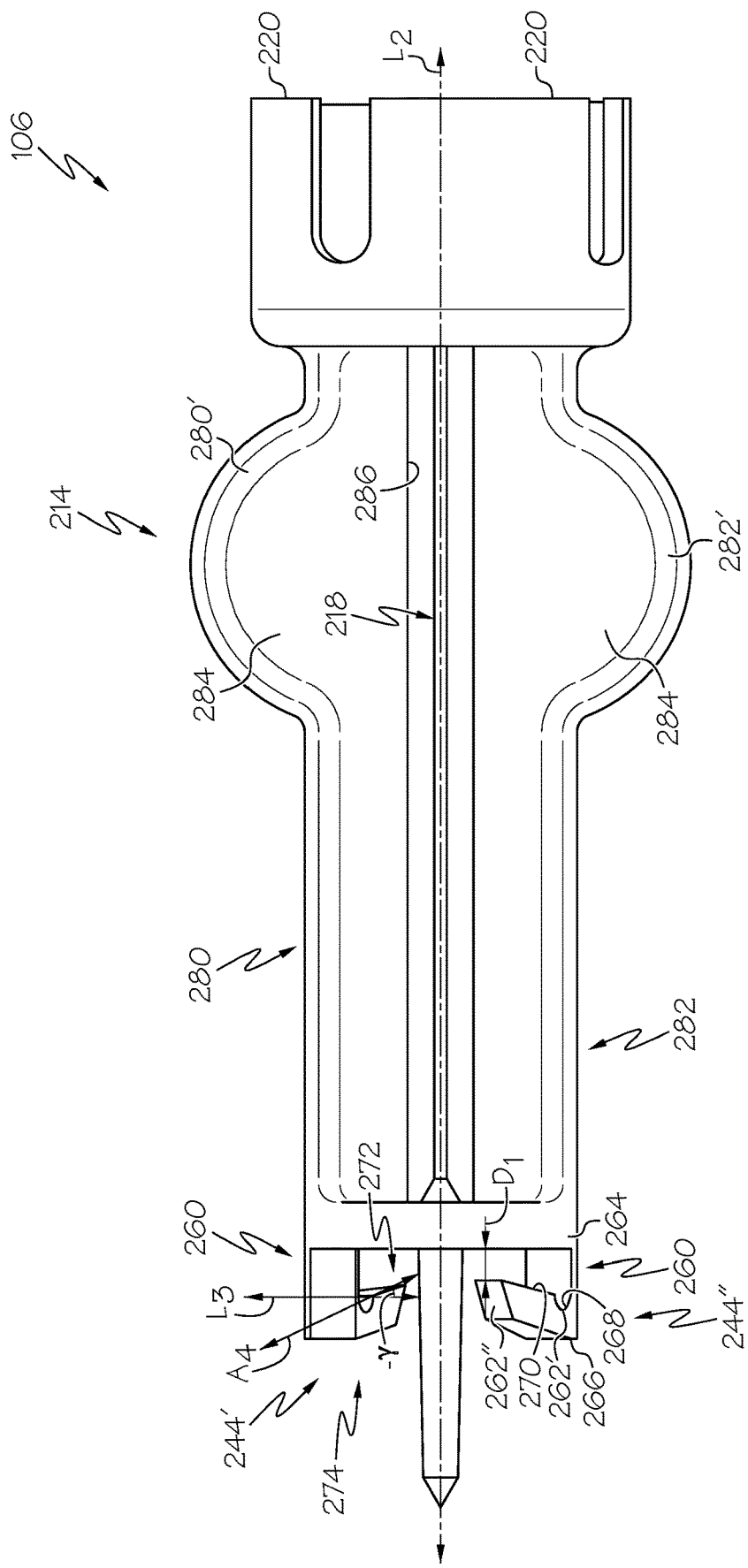
FIG. 13 is a side view of the transfer guard of the system of FIG. 1.

With reference to FIG. 13, each of the locking members 244', 244" include a stem 260 and a locking arm 262. Each stem 260 has a first stem end 264 opposite a second stem end 266. The first stem end 264 is coupled to the second surface 248 of the second base 240, and the second stem end 266 is coupled to the locking arm 262. The stem 260 generally extends outwardly along an axis that is substantially parallel to the longitudinal axis L2 of the transfer guard 106. The stem 260 extends for a length that enables the locking arm 262 to engage with the first ramp surfaces 200 of the respective locking projections 192', 192".

Each locking arm 262 is coupled to the second stem end 266. The locking arms 262 extend outwardly from the second stem end 266 so as to at least partially follow the perimeter or circumference of the second base 240. Stated another way, the locking arms 262 are arcuate, and extend outward from the second stem end 266 so as to be spaced a distance apart from the second surface 248 of the second base 240. The locking arms 262 each include a notch 268 and a second ramp surface 270. The notch 268 and the second ramp surface 270 are defined on a first arm side 272, which is opposite a second arm side 274. The notch 268 is defined at a first end 262' of the locking arms 262, and the second ramp surface 270 extends from the notch 268 to a second end 262" of the locking arms 262.

The notch 268 is defined at the first end 262' to enable the locking arms 262 to move between a first position and a second position. Generally, the notch 268 is a groove, which reduces a thickness of each of the locking arms 262 at the first end 262' to provide each of the locking arms 262 with flexibility to move the locking members 244', 244" between the first position and the second position. Generally, the locking members 244', 244" are in the first position when the locking arms 262 are unbiased or in a neutral, unflexed position, as is shown in FIG. 13. In the first position, the second end 262" of each of the locking arms 262 is spaced a first distance D1 from the second surface 248 of the second base 240. In the second position, the locking members 244', 244" are flexed, biased or expanded outwardly away from the second surface 248 such that the second end 262" of each of the locking arms 262 is spaced a second distance D2 (FIG. 2) away from the second surface 248. The second distance D2 is generally greater than the first distance D1 such that when the locking arms 262 are disengaged with the respective locking projections 192', 192" of the interface 152, the locking arms 262 return to the first position and substantially prevent the reassembly of the transfer guard 106 to the interface 152. Thus, the locking members 244', 244" cooperate with the locking projections 192', 192" to substantially prevent the reuse of the transfer guard 106.

The second ramp surface 270 is defined on the first arm side 272 of the locking arm 262 so as to extend from the notch 268 to the second end 262". In this example, the second ramp surface 270 has an incline that mates with the first ramp surface 200 of the respective locking projections 192', 192" such that each of the locking arms 262 may be coupled to the locking projections 192', 192" to enable a filling of the reservoir 118.

Generally, the second ramp surface 270 extends along an axis A4, which is substantially transverse or oblique to a line L3 that lies along a plane defined through the locking arm 262. In this example, the second ramp surface 270 is at an angle −γ of about negative 5 to about negative 20 degrees relative to the second projection end 198. It should be noted that the second ramp surface 270 need not extend along a line, but rather, may be contoured or curved, depending upon the force requirements necessary for the coupling and uncoupling of the transfer guard 106 from the interface 152. It will be understood that the use of the first ramp surface 200 and the second ramp surface 270 is merely exemplary, as any suitable cooperating engagement surfaces may be defined, such as mating threads, etc.

The body 214 of the transfer guard 106 can fluidly interconnect or couple the fluid reservoir 102 and the vial 108 to each other. The body 214 may be elongated along the longitudinal axis L2, however, the body 214 can have any desired shape to fluidly interconnect or couple the fluid reservoir 102 and the vial 108 together. In this example, the body 214 includes a first member 280, a second member 282 and defines a central body bore 286 between the first member 280 and the second member 282.

The first member 280 and the second member 282 are substantially planar, but may include a thickened ridge 280', 282' about a perimeter of the respective first member 280 and second member 282 to facilitate a user's handling of the transfer guard 106. The first member 280 and the second member 282 are substantially symmetric about a plane defined by the longitudinal axis L2. The first member 280 and the second member 282 each include a graspable portion 284, which projects outwardly a reminder of the first member 280 and the second member 282. The graspable portion 284 enables a user to manipulate the transfer guard 106, which aids in coupling the vial 108 to the transfer guard 106.

The central body bore 286 is defined between the first member 280 and the second member 282. The central body bore 286 extends along the longitudinal axis L2, and is sized to enable the first piercing member 218 to pass through the transfer guard 106 from the base 222 to the second base 240. Thus, with reference to FIG. 3, the central body bore 286 is generally in communication with the bore 228 of the base 222 and the second bore 250 of the second base 240.

With reference to FIG. 1, the vial 108 can comprise any suitable vial for storing a fluid F. In one example, the vial 108 stores insulin, and defines a chamber 300 for storing the fluid. With reference to FIG. 1, the chamber 300 narrows or necks to the flange 226. The flange 226 may be coupled to the first end 210 of the transfer guard 106. The flange 226 defines a vial passageway 302. The vial passageway 302 provides a fluid flow path out of the chamber 300, and is closed with a septum 304. The septum 304 is disposed in the flange 226 and serves to prevent the ingress and egress of fluids out of the chamber 300 of the vial 108. The septum 304 is pierceable with the first piercing member 218 to enable fluid flow out of the vial 108.

With reference to FIG. 3, in order to assemble or couple the transfer guard 106 to the fluid reservoir 102, in one example, with the stopper 150, the barrel portion 110, the interface 152 and the transfer guard 106 formed, the stopper 150 may be pre-slit to define the central slit 160. The interface 152 is coupled about the base 174 of the stopper 150 such that the flange 176 is received within the counterbore 208 (FIG. 7). With the interface 152 coupled to the stopper 150, a suitable tool, such as a spreading tool, may be coupled to the second end 212 of the transfer guard 106 to move the locking members 244', 244" from the first position to the second position. In the second position, the locking members 244', 244" are flexed, biased or expanded outward away from the second surface 248 such that the locking arms 262 are spaced from the second surface 248 by the second distance D2 (FIG. 2). With the locking members 244', 244" in the second position, the transfer guard 106 is coupled to the interface 152 by rotating the transfer guard 106 until the second ramp surfaces 270 substantially contact the wall 206 of the locking projections 192', 192". The coupling of the transfer guard 106 to the interface 152 advances the second piercing member 242 through the central slit 160 until the second piercing member 242 extends outwardly from the first stopper surface 162.

With the transfer guard 106 coupled to the interface 152, and the interface 152 coupled to the stopper 150, the stopper 150 is inserted into the barrel portion 110 through the open circumference of the barrel portion 110 at the second end 116. Generally, the stopper 150 is inserted into the barrel portion 110 until the stopper 150 contacts or is adjacent to the second side 129 of the end wall 127 (FIG. 3A). The second piercing member 242 may pass into the needle passage 134, but does not pierce the septum 136. By advancing the stopper 150 coupled to the transfer guard 106 to the first end 114 of the barrel portion 110, the movement of the stopper 150 from the first end 114 to the second end 116 (FIG. 2) while fluidly coupled to the vial 108 by the transfer guard 106 will cause the fluid F to flow from the vial 108 into the reservoir 118 to fill the reservoir 118. Thus, while not illustrated in FIG. 1, the fluid reservoir 102 and the transfer guard 106 may be packaged for the user such that the fluid reservoir 102 and the transfer guard 106 are coupled together, with the locking members 244', 244" of the transfer guard 106 coupled to the locking projections 192', 192" of the interface 152.

With the fluid reservoir 102 assembled and coupled to the transfer guard 106, the fluid reservoir 102 and the vial 108 may be packaged together such that the fluid transfer system 100 may form a kit to be used by a user to fill the fluid reservoir 102. Once the fluid transfer system 100 is received or obtained by a user, the user may begin a filling operation. In one example, the user may couple the vial 108 to the first end 210 of the transfer guard 106 such that the first piercing member 218 pierces the septum 304 of the vial 108, and thereby establishes a fluid flow path from the vial 108, through the first piercing member 218 and through the second piercing member 242 into the reservoir 118, as shown in FIG. 2. With continued reference to FIG. 2, the user grasps the graspable portion 284 and may apply a force F2 to the transfer guard 106 to move the stopper 150 from the first end 114 of the barrel portion 110 (as shown in FIG. 3A) to the second end 116 (as shown in FIG. 3). The movement of the stopper 150 from the first end 114 to the second end 116 fills the reservoir 118 with the fluid F from the vial 108 via the fluid flow path defined by the first piercing member 218 and the second piercing member 242 of the transfer guard 106 (FIG. 2).

Generally, as the fluid F flows from the vial 108 through the first piercing member 218 and the second piercing member 242, the fluid F exits into the reservoir 118 via the cross-bore 252 defined in the second piercing member 242 (FIG. 12). The sideways flow path from the cross-bore 252 may reduce an amount of air trapped between the second piercing member 242 and the stopper 150. Moreover, the second side 129 guides any trapped air or "bubbles" along the surface 144 to the trap 142. The trap 142 may capture trapped air or "bubbles" and substantially eliminate trapped air or "bubbles" exiting the reservoir 118 via the delivery port 120. In addition, as the transfer guard 106 is coupled to the stopper 150, the risk of wetting vent ports associated with the infusion set coupled to the delivery port 120 is substantially eliminated.

Figure 14:
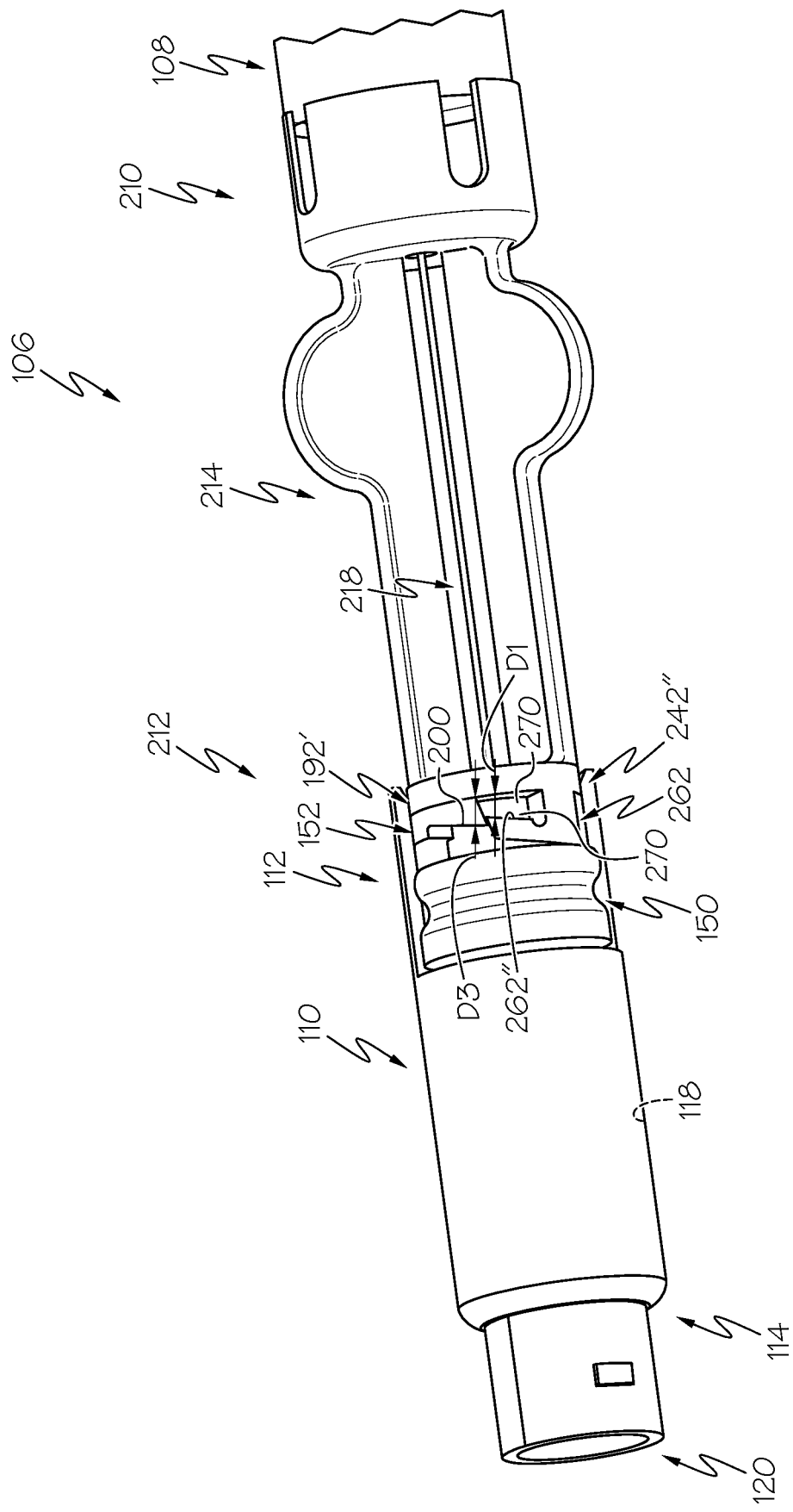
FIG. 14 is perspective view of the system of FIG. 1 assembled to fill the fluid reservoir of the fluid infusion device, with the pair of locking members of the transfer guard in a first position.

Once the stopper 150 is near the second end 116, such that the second base 240 is adjacent to a terminal end 116' of the second end 116, the reservoir 118 is substantially filled with the fluid F. The user may then uncouple the transfer guard 106 from the interface 152. In order to uncouple the transfer guard 106, the user may apply a torque T to the body 214 of the transfer guard 106 to rotate the transfer guard 106 relative to the interface 152. The applied torque T causes the second ramp surface 270 of the locking arms 262 to move up the first ramp surface 200 of the locking projections 192', 192" until the locking members 244', 244" no longer contact the locking projections 192', 192", as shown in FIG. 14. With the locking members 244', 244" disengaged from the locking projections 192', 192", the locking members 244', 244" move from the second position to the first position. In the first position, the first distance D1 between the second end 262" of each of the locking members 244', 244" is less than a distance or length D3 of the second ramp end 200" of each of the first ramp surfaces 200 such that the locking members 244', 244" cannot reengage with or be recoupled to the locking projections 192', 192". Stated another way, the length D3 of the second ramp end 200" is greater than the first distance D1 between the second end 262" and the second side 248 such that the transfer guard 106 cannot be reengaged with the interface 152. Thus, once the user applies the torque T to uncouple the transfer guard 106 from the interface 152, the user may not recouple or reconnect the transfer guard 106 to the interface 152. With the transfer guard 106 uncoupled from the interface 152, the transfer guard 106 may be removed from the second end 116 of the fluid reservoir 102, and the central slit 160 of the stopper 150 may close due to the resilient material from which the stopper 150 is composed. The fluid reservoir 102 may then be coupled to the fluid infusion device 104.

The fluid transfer system 100 enables the filling of the fluid reservoir 102 while substantially eliminating the risk of wetting one or more vent ports associated with an infusion set that is coupled to the delivery port 120 as the fluid F is introduced to the fluid reservoir 102 at the second end 116. In addition, by using the second piercing member 242 coupled to the stopper 150, an amount of air that enters the reservoir 118 and becomes trapped during the filling operation is reduced. Moreover, any air or "bubbles" that may enter the reservoir 118 during the filling operation may follow the ramp defined by the surface 144 of the second side 129 and become trapped in the trap 142 (FIG. 4). By trapping the "bubbles" in the trap 142, the fluid reservoir 102 substantially eliminates and prevents air from exiting the fluid reservoir 102 via the delivery port 120. Further, the cooperation between the locking projections 192', 192" of the interface 152 and the locking members 244', 244" of the transfer guard 106 ensure that the user may only use the transfer guard 106 one time. In this regard, as special tools are required to open up the locking members 244', 244" of the transfer guard 106 to couple the locking members 244', 244" to the locking projections 192', 192" of the interface 152, a user cannot simply recouple the transfer guard 106 to the interface 152 once the transfer guard 106 has been uncoupled from the interface 152 at the completion of the filling operation. Thus, the system 100 enables the reservoir 118 to be filled with fluid from the vial 108, for example, insulin, with little to no trapped air or "bubbles," while inhibiting the reuse of the transfer guard 106.

Figure 15:
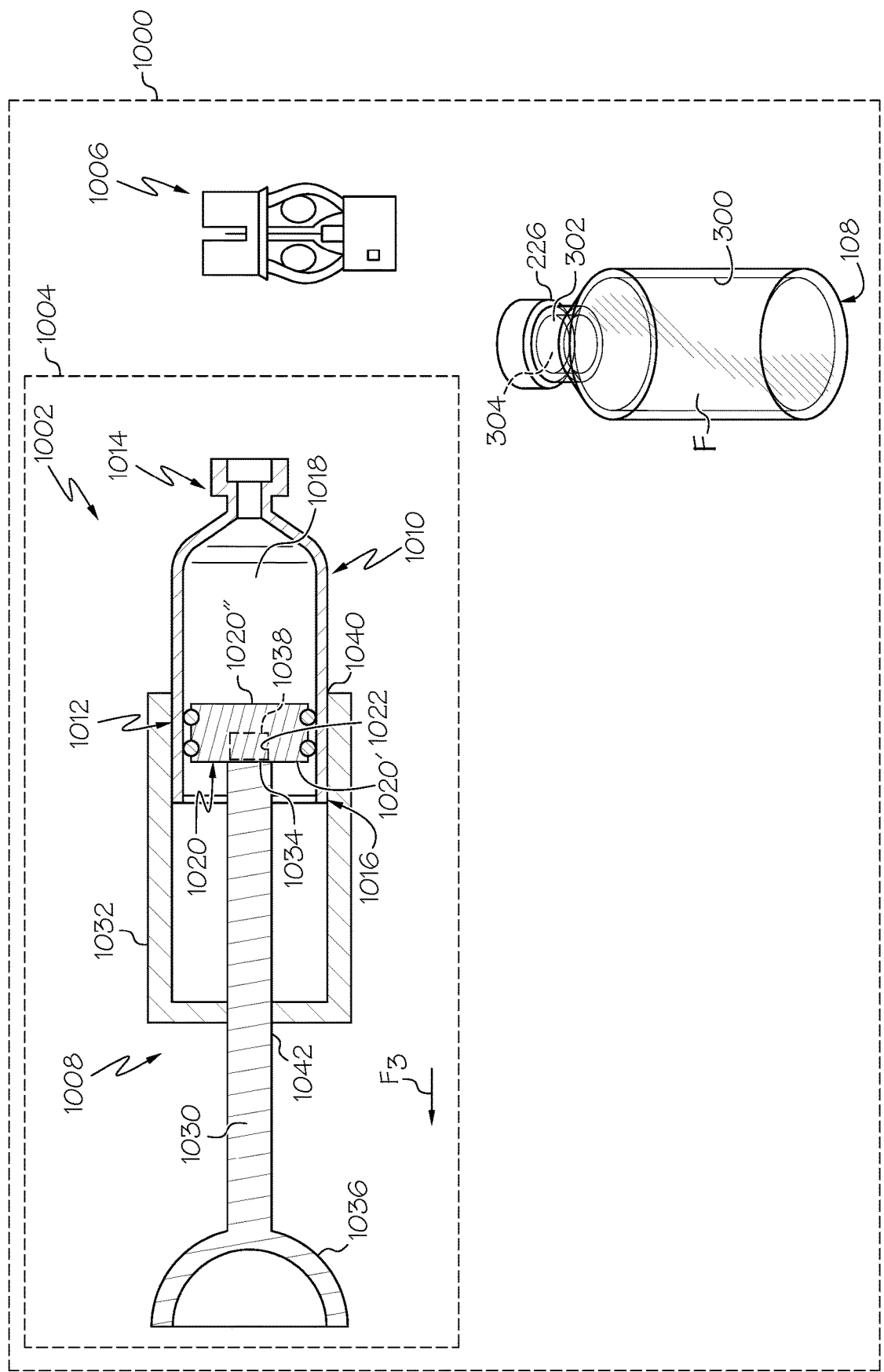
FIG. 15 is a perspective view of another exemplary fluid reservoir of a fluid infusion device and another exemplary system for filling the fluid reservoir of the fluid infusion device according to various teachings of the present disclosure.

It should be noted that the configuration of the fluid transfer system 100 as described herein is not limited to the configuration shown in FIGS. 1-14. In this regard, with reference to FIG. 15, a fluid transfer system 1000 is shown. As the fluid transfer system 1000 is similar to the fluid transfer system 100 described with regard to FIGS. 1-14, the same reference numerals will be used to denote the same features.

In this example, the fluid transfer system 1000 is for filling a fluid reservoir 1002 of the fluid infusion device 104. The system 1000 includes the fluid reservoir 1002 of the fluid infusion device 104, a transfer device or guard 1006, the vial 108 and a pull-rod 1008. The transfer guard 1006 may be commercially available from Medtronic MiniMed, Inc. of Northridge, Calif., and thus, will not be discussed in great detail herein. One or more components of the system 1000 can be packaged together in suitable packaging for use as a kit by a consumer or user. The system 1000 enables the user to fill the fluid reservoir 1002 of the fluid infusion device 104 with all or a portion of the contents of the vial 108 while reducing a risk of wetting one or more vent ports associated with the infusion set coupled to the fluid reservoir 1002 as will be discussed in greater detail herein.

The fluid reservoir 1002 includes a first portion or barrel portion 1010 and a second portion or plunger portion 1012. Generally, the barrel portion 1010 includes a first end 1014, a second end 1016 and a reservoir 1018 defined between the first end 1014 and the second end 1016. The first end 1014 defines a fluid flow path out of the reservoir 1018 when coupled to a set connector of an infusion set, and generally includes a septum (not shown). The second end 1016 is circumferentially open, and receives the plunger portion 1012. Generally, the plunger portion 1012 is movable or slidable within the reservoir 1018 to fill the reservoir 1018 with fluid or advance fluid out of the reservoir 1018 via the fluid flow path defined at the first end 1014.

In this example, the plunger portion 1012 includes a stopper 1020. The stopper 1020 is coupled to an interior wall 1018' of the reservoir 1018 and is movable relative to the reservoir 1018 by a drive system of the fluid infusion device 104 to advance fluid out of the reservoir 1018. The stopper 1020 may also be coupled to the pull-rod 1008 to draw fluid into the reservoir 1018 during a filling operation. In this example, the stopper 1020 includes a coupling feature 1022, which is defined on a first side 1020' of the stopper 1020. The first side 1020' of the stopper 1020 is substantially opposite a second side 1020" of the stopper 1020 that disposed within the reservoir 1018. The coupling feature 1022 is any suitable coupling feature, such as a threaded bore, a keyed interface, etc., which couples the stopper 1020 to the pull-rod 1008. By coupling the stopper 1020 to the pull-rod 1008, the stopper 1020 may be moved relative to the barrel portion 1010 to fill the reservoir 1018 with the fluid F from the vial 108.

The pull-rod 1008 generally includes a rod 1030 and a sleeve 1032. The rod 1030 has a first end 1034 coupled to the stopper 1020, and a second, opposite end 1036. The first end 1034 includes a second coupling feature 1038 that cooperates with the coupling feature 1022 of the stopper 1020 to couple the rod 1030 to the stopper 1020. In the example of the coupling feature 1022 comprising a threaded bore, the second coupling feature 1038 comprises a plurality of threads, which matingly engage with the threaded bore of the coupling feature 1022 to couple the stopper 1020 to the rod 1030. The second end 1036 of the rod 1030 comprises a graspable portion, which may be manipulated by a user to move the stopper 1020 and thereby fill the reservoir 1018.

The sleeve 1032 defines an opening 1040, which is sized and shaped to form a tight fit with reduced clearance about the perimeter or circumference of the plunger portion 1012 of the fluid reservoir 1002. In one example, the sleeve 1032 may form an interference fit with the second end 1016 of the fluid reservoir 1002. The sleeve 1032 also defines a rod bore 1042, which enables the rod 1030 to be movable relative to the sleeve 1032.

In order to use the fluid transfer system 1000 to fill the fluid reservoir 1002, the sleeve 1032 is positioned about the second end 1016 of the barrel portion 1010. The rod 1030 is advanced through the rod bore 1042, and the second coupling feature 1038 is coupled to or engaged with the coupling feature 1022 of the stopper 1020 to couple the stopper 1020 to the rod 1030. The transfer guard 1006 is coupled to the first end 1014 of the barrel portion 1010 such that a piercing member of the transfer guard 1006 pierces the septum of the fluid reservoir 1002, and the vial 108 is coupled to the transfer guard 1006 such that a piercing member of the transfer guard 1006 pierces the septum 304 of the vial 108.

With the fluid reservoir 102 and the vial 108 in fluid communication via the transfer guard 1006, a force F3 is applied to the rod 1030 to move the stopper 1020 from the first end 1014 to the second end 1016. As the stopper 1020 moves toward the second end 1016, the fluid F from the vial 108 enters the reservoir 1018. The force F3 is applied to the stopper 1020 until the stopper 1020 is near or at the second end 1016. Once the stopper 1020 is near or at the second end 1016, the reservoir 1018 is substantially filled with the fluid F and the rod 1030 may be uncoupled from the stopper 1020. The sleeve 1032 is then removed from the fluid reservoir 1002, and the fluid reservoir 1002 may be coupled to the fluid infusion device 104.

Thus, the fluid transfer system 1000 enables the filling of the fluid reservoir 1002 while substantially eliminating the risk of wetting one or more vent ports associated with an infusion set coupled to the delivery port by coupling the pull-rod 1008 to the stopper 1020. In addition, as the pull-rod 1008 may not be in contact with the fluid, such as insulin, during the filling of the fluid reservoir 1002, the pull-rod 1008 may be a durable component, such that the pull-rod 1008 may be used multiple times (i.e. reused) to fill the fluid reservoir 1002. This may reduce a user's cost associated with filling the fluid reservoir 1002.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A fluid reservoir for a fluid infusion device, comprising:
    a first portion that has a first end and a second end, the first end includes a first surface that includes a fluid delivery port and a second surface that defines a ramp that extends from the fluid delivery port to an annular groove, the annular groove defined about a perimeter of the second surface, with a sharp corner defined at an outer end of the ramp that transitions from the ramp to the annular groove, the annular groove defined beyond the second surface in a direction of fluid flow from the fluid reservoir, the ramp and the annular groove cooperate to retain bubbles within the fluid reservoir;
    a second portion received in the second end of the first portion and movable within the first portion from the second end to the first end; and
    a fluid chamber defined between the first portion and the second portion.

2. The fluid reservoir of claim 1, wherein the ramp and the annular groove are disposed within the fluid chamber.

3. The fluid reservoir of claim 1, wherein the first end includes an end wall having the first surface and the second surface and the fluid delivery port includes a needle passage that extends through the end wall to define a fluid flow path from the fluid chamber through the fluid delivery port, and the ramp extends along the second surface from the needle passage to the annular groove.

4. The fluid reservoir of claim 1, wherein the second portion includes a stopper that is movable within the first portion, the stopper having a first stopper end and a second stopper end, the first stopper end has a contour that mates with the ramp of the second surface such that the stopper is positionable against the second surface to dispense fluid in the fluid chamber through the fluid delivery port.

5. The fluid reservoir of claim 4, wherein the stopper is a monolithic component, the stopper has a sidewall that includes at least one sealing surface that contacts an interior surface of the first portion, and the at least one sealing surface is monolithic with the stopper.

6. The fluid reservoir of claim 1, wherein the fluid delivery port further comprises a septum chamber to receive a septum, and the septum chamber includes a radial flange to retain the septum within the septum chamber.

7. A fluid reservoir for a fluid infusion device, comprising:
    a barrel portion that has a first end and a second end, the first end includes a first surface that includes a fluid delivery port and a second surface that defines a ramp that extends from the fluid delivery port to an annular groove, the annular groove defined about a perimeter of the second surface, with a sharp corner defined at an outer end of the ramp that transitions from the ramp to the annular groove, the annular groove defined beyond the second surface in a direction of fluid flow from the fluid reservoir, the ramp and the annular groove cooperate to retain bubbles within the fluid reservoir;
    a plunger portion received in the second end of the barrel portion and movable within the barrel portion from the second end to the first end; and
    a fluid chamber defined between the barrel portion and the plunger portion, and the ramp and the annular groove are disposed within the fluid chamber.

8. The fluid reservoir of claim 7, wherein the first end includes an end wall having the first surface and the second surface and the fluid delivery port includes a needle passage that extends through the end wall to define a fluid flow path from the fluid chamber through the fluid delivery port, and the ramp extends along the second surface from the needle passage to the annular groove.

9. The fluid reservoir of claim 7, wherein the plunger portion includes a stopper that is movable within the barrel portion, the stopper having a first stopper end and a second stopper end, the first stopper end has a contour that mates with the ramp of the second surface such that the stopper is positionable against the second surface to dispense fluid in the fluid chamber through the fluid delivery port.

10. The fluid reservoir of claim 9, wherein the stopper is a monolithic component, the stopper has a sidewall that includes at least one sealing surface that contacts an interior surface of the barrel portion, and the at least one sealing surface is monolithic with the stopper.

11. The fluid reservoir of claim 7, wherein the fluid delivery port further comprises a septum chamber to receive a septum, and the septum chamber includes a radial flange to retain the septum within the septum chamber.

12. A fluid reservoir for a fluid infusion device, comprising:
   a barrel portion that has a first end and a second end, the first end includes an end wall having a first surface and a second surface, the first surface includes a fluid delivery port and the second surface defines a ramp, with an annular groove defined about a perimeter of the second surface, the ramp extending from the fluid delivery port to the annular groove, with a sharp corner defined at an outer end of the ramp that transitions from the ramp to the annular groove, the annular groove defined beyond the second surface in a direction of fluid flow from the fluid reservoir, the ramp and the annular groove cooperating to retain bubbles within the fluid reservoir;
   a plunger portion having a monolithic stopper received in the second end of the barrel portion and movable within the barrel portion from the second end to the first end, the stopper having a first stopper end opposite a second stopper end and a slit defined through the stopper from the first stopper end to the second stopper end, the first stopper end having a lip that projects outwardly from the first stopper end to be received within the annular groove; and
   a fluid chamber defined between the barrel portion and the plunger portion.

13. The fluid reservoir of claim 12, wherein the stopper has a contour that mates with the ramp of the second surface such that the stopper is positionable against the second surface to dispense fluid in the fluid chamber through the fluid delivery port.

14. The fluid reservoir of claim 12, wherein the fluid delivery port includes a needle passage that extends through the end wall to define a fluid flow path from the fluid chamber through the fluid delivery port, and the ramp extends along the second surface from the needle passage to the annular groove.

* * * * *